US010095487B1

(12) United States Patent
Venkatesan et al.

(10) Patent No.: US 10,095,487 B1
(45) Date of Patent: *Oct. 9, 2018

(54) DATA TYPE VISUALIZATION

(71) Applicant: The MathWorks, Inc., Natick, MA (US)

(72) Inventors: Vaidehi Venkatesan, Waltham, MA (US); Thomas A. Bryan, Westborough, MA (US); Julia P. Wall, West Roxbury, MA (US)

(73) Assignee: The MathWorks, Inc., Natick, MA (US)

( * ) Notice: Subject to any disclaimer, the term of this patent is extended or adjusted under 35 U.S.C. 154(b) by 57 days.

This patent is subject to a terminal disclaimer.

(21) Appl. No.: 15/339,660

(22) Filed: Oct. 31, 2016

Related U.S. Application Data

(63) Continuation-in-part of application No. 15/149,876, filed on May 9, 2016, which is a continuation of application No. 14/486,241, filed on Sep. 15, 2014, now Pat. No. 9,335,979.

(51) Int. Cl.
G06F 9/44 (2018.01)
G06F 8/34 (2018.01)
G06F 8/41 (2018.01)
G06F 3/0481 (2013.01)
G06F 19/28 (2011.01)

(52) U.S. Cl.
CPC .............. *G06F 8/34* (2013.01); *G06F 3/0481* (2013.01); *G06F 8/433* (2013.01); *G06F 19/28* (2013.01)

(58) Field of Classification Search
CPC .... G06F 3/0481; G06F 8/316; G06F 19/3443; G06F 19/28; G06F 8/34; G06T 11/206; G06Q 10/06314; G06Q 40/06; G06H 50/70
See application file for complete search history.

(56) References Cited

U.S. PATENT DOCUMENTS

| 5,432,942 | A | 7/1995 | Trainer |
| 6,854,001 | B2 | 2/2005 | Good et al. |
| 7,174,536 | B1 | 2/2007 | Kothari et al. |
| 7,216,116 | B1 | 5/2007 | Nilsson et al. |
| 8,365,088 | B1 | 1/2013 | Rodriguez et al. |
| 9,335,979 | B1 | 5/2016 | Bryan et al. |
| 2005/0096950 | A1* | 5/2005 | Caplan ............. G06Q 10/06314 705/7.24 |

(Continued)

Primary Examiner — Yuan Vu
(74) Attorney, Agent, or Firm — Harrity & Harrity, LLP

(57) ABSTRACT

A device may obtain program code, determine variables based on the program code, execute or analyze the program code, and determine values of the variables based on the executing or analyzing. The device may determine a range for each variable based on positions of at least one significant digit for the values. The range may be determined based on a count of a quantity of occurrences of the at least one significant digit for the values. The device may determine relationships between the variables based on the executing or analyzing, and may determine one or more effects on the range for the variables based on the relationships between the variables. The device may generate a visualization that presents the range for the variables, the relationships between the variables, and the one or more effects on the range for the variables, and may provide the visualization for display.

20 Claims, 31 Drawing Sheets

(56) References Cited

U.S. PATENT DOCUMENTS

| | | |
|---|---|---|
| 2006/0106783 A1 | 5/2006 | Saffer et al. |
| 2006/0190184 A1* | 8/2006 | Sasinowski ............. G06F 19/28 702/19 |
| 2010/0030518 A1 | 2/2010 | Weber |
| 2010/0122240 A1 | 5/2010 | Matsuo et al. |
| 2010/0191678 A1* | 7/2010 | Steed ................... H06T 11/206 706/11 |
| 2011/0191343 A1* | 8/2011 | Heaton ................. G16H 50/70 707/737 |

* cited by examiner

| | $2^6$ | $2^5$ | $2^4$ | $2^3$ | $2^2$ | $2^1$ | $2^0$ | . | $2^{-1}$ | $2^{-2}$ | $2^{-3}$ | $2^{-4}$ | $2^{-5}$ |
|---|---|---|---|---|---|---|---|---|---|---|---|---|---|
| $y(1) = 1$ | 0 | 0 | 0 | 0 | 0 | 0 | ①  | . | 0 | 0 | 0 | 0 | 0 |
| $y(2) = 2.25$ | 0 | 0 | 0 | 0 | 0 | ① | 0 | . | 0 | ⊡ | 0 | 0 | 0 |
| $y(3) = 4$ | 0 | 0 | 0 | 0 | ① | 0 | 0 | . | 0 | 0 | 0 | 0 | 0 |
| $y(4) = 6.25$ | 0 | 0 | 0 | 0 | ① | ① | 0 | . | 0 | ⊡ | 0 | 0 | 0 |
| $y(5) = 9$ | 0 | 0 | 0 | ① | 0 | 0 | ⊡ | . | 0 | 0 | 0 | 0 | 0 |
| $y(6) = 12.25$ | 0 | 0 | 0 | ① | ① | 0 | 0 | . | 0 | ⊡ | 0 | 0 | 0 |
| $y(7) = 16$ | 0 | 0 | ① | 0 | 0 | 0 | 0 | . | 0 | 0 | 0 | 0 | 0 |
| $y(8) = 20.25$ | 0 | 0 | ① | 0 | ① | 0 | 0 | . | 0 | ⊡ | 0 | 0 | 0 |
| $y(9) = 25$ | 0 | 0 | ① | ① | 0 | 0 | ⊡ | . | 0 | 0 | 0 | 0 | 0 |
| $y(10) = 30.25$ | 0 | 0 | ① | ① | ① | ① | 0 | . | 0 | ⊡ | 0 | 0 | 0 |
| msb count | 0 | 0 | 4 | 2 | 2 | 1 | 2 | . | 0 | 0 | 0 | 0 | 0 |
| lsb count | 0 | 0 | 1 | 0 | 1 | 3 | 3 | . | 0 | 5 | 0 | 0 | 0 |
| all bits | 0 | 0 | 4 | 4 | 5 | 3 | 3 | . | 0 | 5 | 0 | 0 | 0 |

Legend:
- bit = binary digit
- msb = most significant bit
- lsb = least significant bit
- ① = most-significant non-zero bit
- ⊡ = least-significant non-zero bit
- ⊞ = most- and least-significant non-zero bit (indicates an exact power of two)

Table 1: BINARY VALUES ASSIGNED TO $y$ IN EXPRESSION $y = x^2$
Values are determined by multiplying the bit value by the non-zero bits. For example, $y(9) = 2^4 + 2^2 + 2^{-1} = 16 + 4 + 0.25 = 20.25$.

FIG. 1D

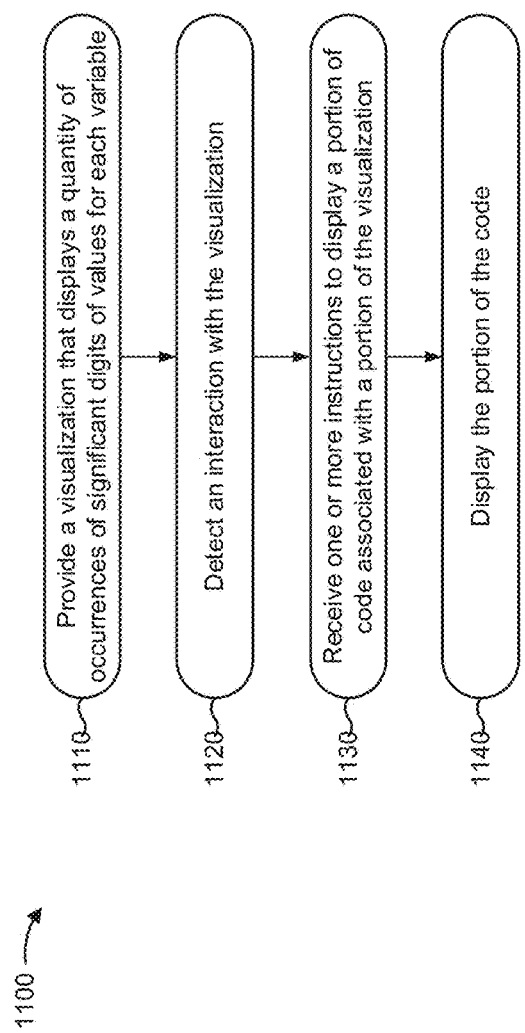

DATA TYPE VISUALIZATION

RELATED APPLICATION

This application is a Continuation-In-Part (CIP) of U.S. patent application Ser. No. 15/149,876, filed on May 9, 2016, which is a continuation of U.S. patent application Ser. No. 14/486,241, filed Sep. 15, 2014 (now U.S. Pat. No. 9,335,979), the disclosures of which are incorporated herein by reference.

BRIEF DESCRIPTION OF THE DRAWINGS

FIGS. 1A-1J are diagrams of an overview of an example implementation described herein;

FIG. 11 is a flow chart of another example process for interacting with a visualization of data types.

DETAILED DESCRIPTION

The following detailed description of example implementations refers to the accompanying drawings. The same reference numbers in different drawings may identify the same or similar elements.

In computer programming, a variable may be used to represent a value that may change over time. A variable may be associated with a data type, which may define characteristics of the possible values represented by the variable. For example, the data type may identify a kind of value (e.g., number, integer, string, Boolean, etc.) and/or a length (e.g., word length, how many digits the value may use) for a variable. The data type assigned to a variable may affect how efficiently memory is allocated. For example, if a variable is assigned 64 bits, but the values represented by the variable do not exceed 32 bits throughout execution of program code (also referred to herein as "code") in which the variable is used, the extra bits may be better allocated elsewhere (e.g., to other variables). The data type may identify a number of significant digits available to be used by a variable to represent a value, and may identify a position of those significant digits (e.g., with respect to a decimal point). The quantity and/or position of significant digits used by a variable to represent values throughout execution of code may be based, at least in part, on a range of values represented by the variable. The range of values may include information such as representable range (e.g., a difference between a maximum value and a minimum value), dynamic range (e.g., a ratio of an absolute value of a largest value and an absolute value of a smallest non-zero value), precision (e.g., a number of significant digits used to represent values), and other such information.

Conventional techniques and applications for determining and presenting data type information for each variable (e.g., a dynamic range for the variable) may be difficult, especially across multiple variables (e.g., some or all variables in a function, a file, a project, or other piece of code) and for unnamed variables (e.g., temporary variables or expressions). Implementations described herein may assist in presenting ranges for multiple variables included in a portion of code, and may allow a user to specify, sort, group, evaluate, and otherwise manipulate a visualization of the ranges and the underlying code.

Figure 1A:
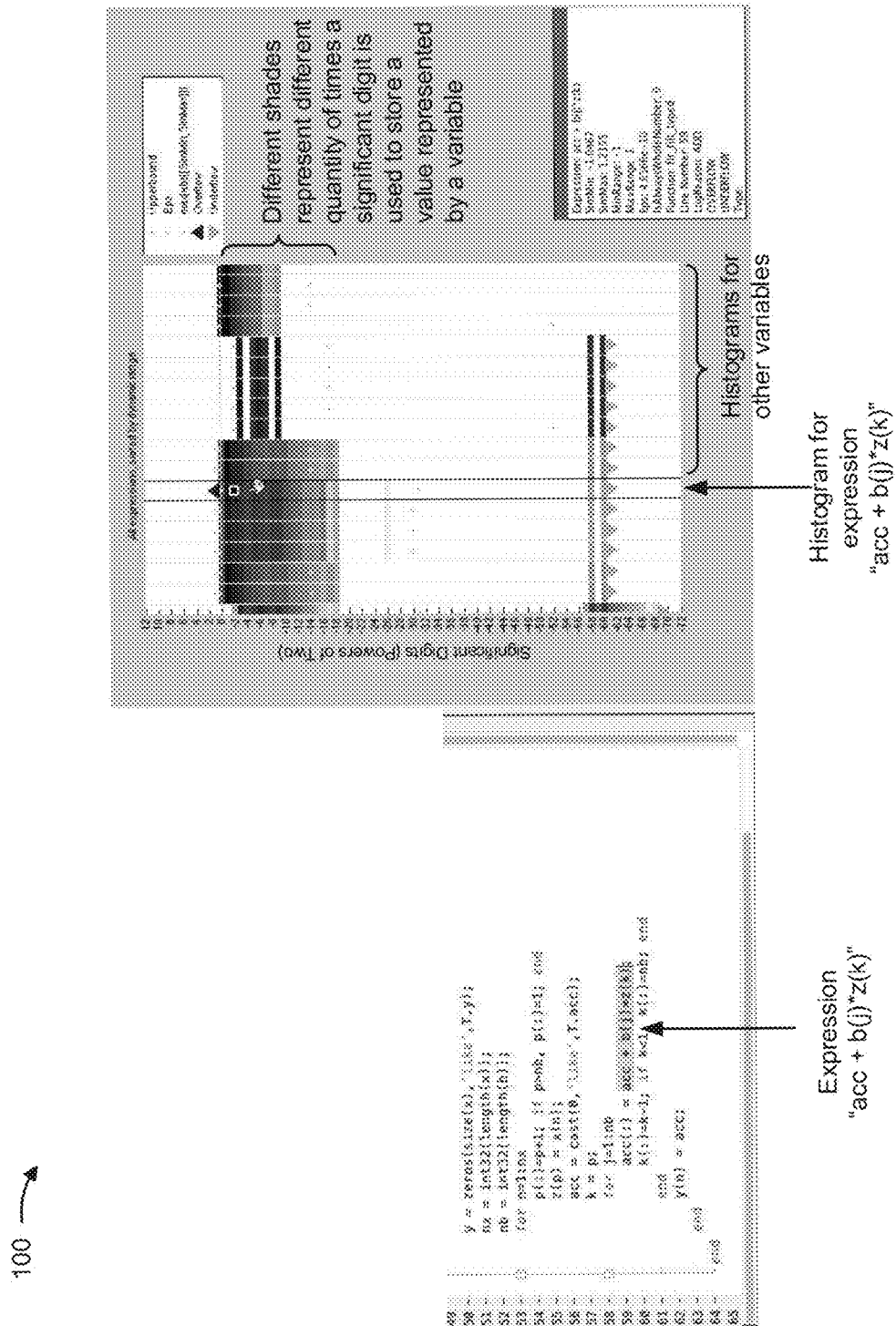
Figure 1B:
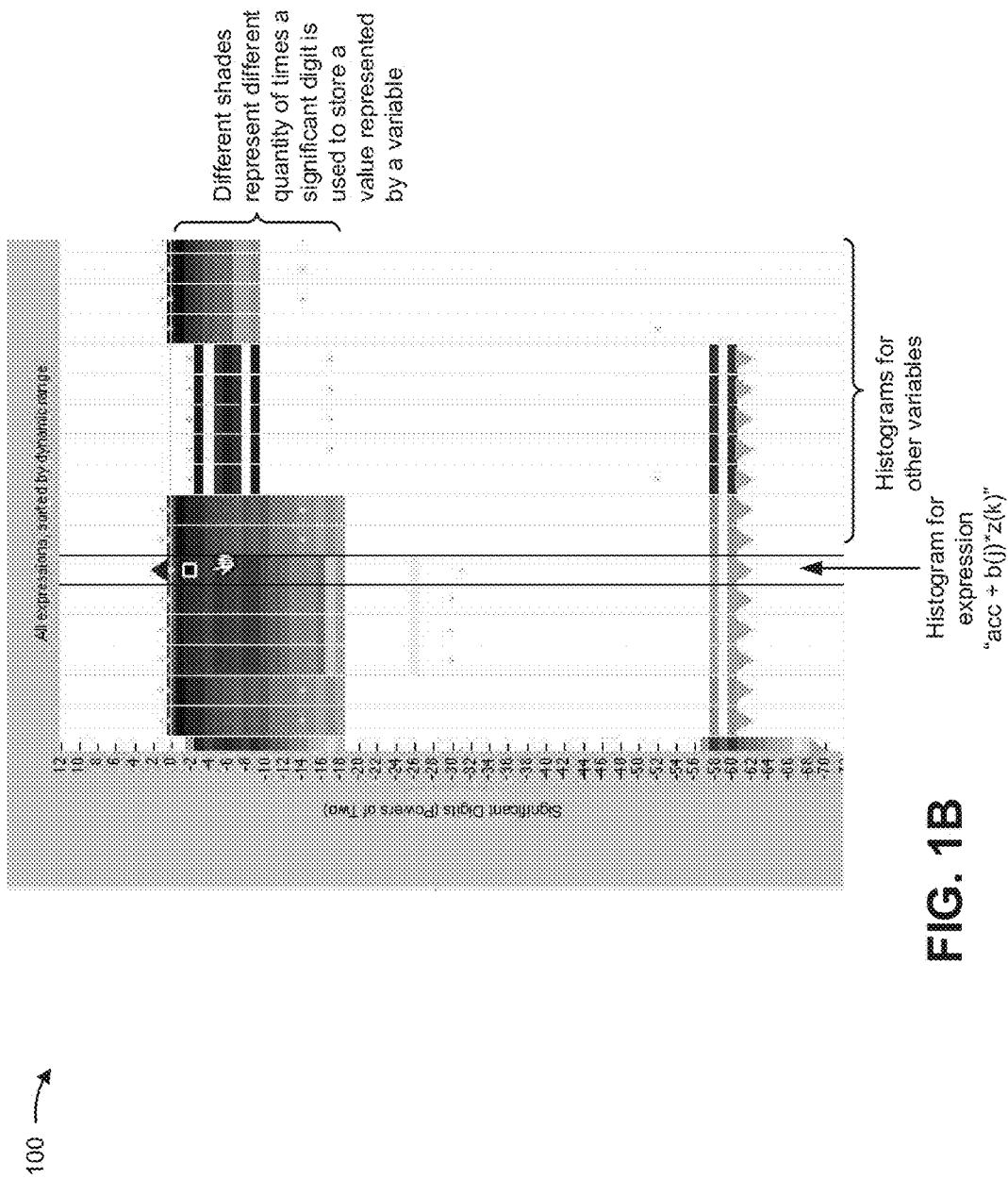

FIGS. 1A-1J are diagrams of an overview of an example implementation 100 described herein. A user may create code, or may wish to analyze code. The user may interact with a user interface to generate a visualization for analyzing the code. As shown in FIGS. 1A and 1B, the visualization may show multiple histograms, each histogram corresponding to a range for a variable included in code. The significant digits used by a variable may be determined by simulating execution of the code, for example, by running multiple test cases on the code. The significant digits used by a variable may also be determined by analyzing the code, for example, by using static analysis and/or by deriving ranges. Each column in the visualization may represent a histogram that shows a quantity of times a significant digit was a most significant digit used by values represented by a variable or an expression including one or more variables. In some embodiments, a least significant digit used by values represented by a variable may be tracked and indicated. In some embodiments, each non-zero significant digit used by values represented by a variable may be tracked and indicated.

Figure 1C:
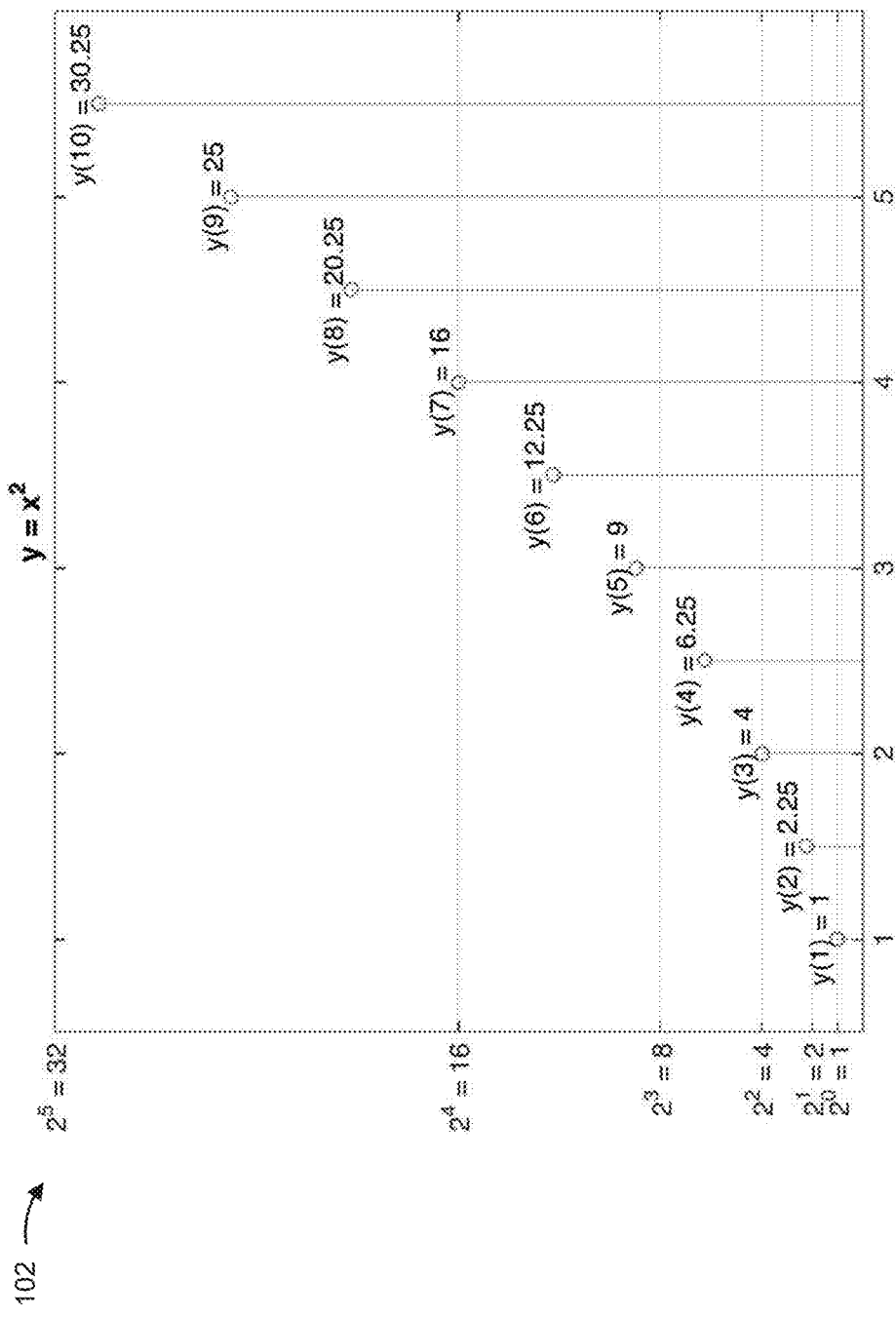

For example, FIG. 1C shows a graph 102 of an example function showing example data assigned to a variable y according to an expression $x^2$. While the function $y=x^2$ is continuous, this example shows a subset of values that are represented by each of the variables. FIG. 1D shows a table 104 with the values represented by the variable y in graph 102. Table 104 shows each of the values for y as well as binary digits used to represent the values. Table 104 also denotes most significant digits, least significant digits, and also counts all digits used to represent each of the values. While table 104 shows binary digits (e.g., bits), other digits may also be used (e.g., base 10, hexadecimal, etc.). While table 104 shows counts for non-zero significant digits, in some embodiments significant digits that are zero may also be counted, for example, if a zero significant digit is between a most and least significant digit used in a value.

Figure 1E:
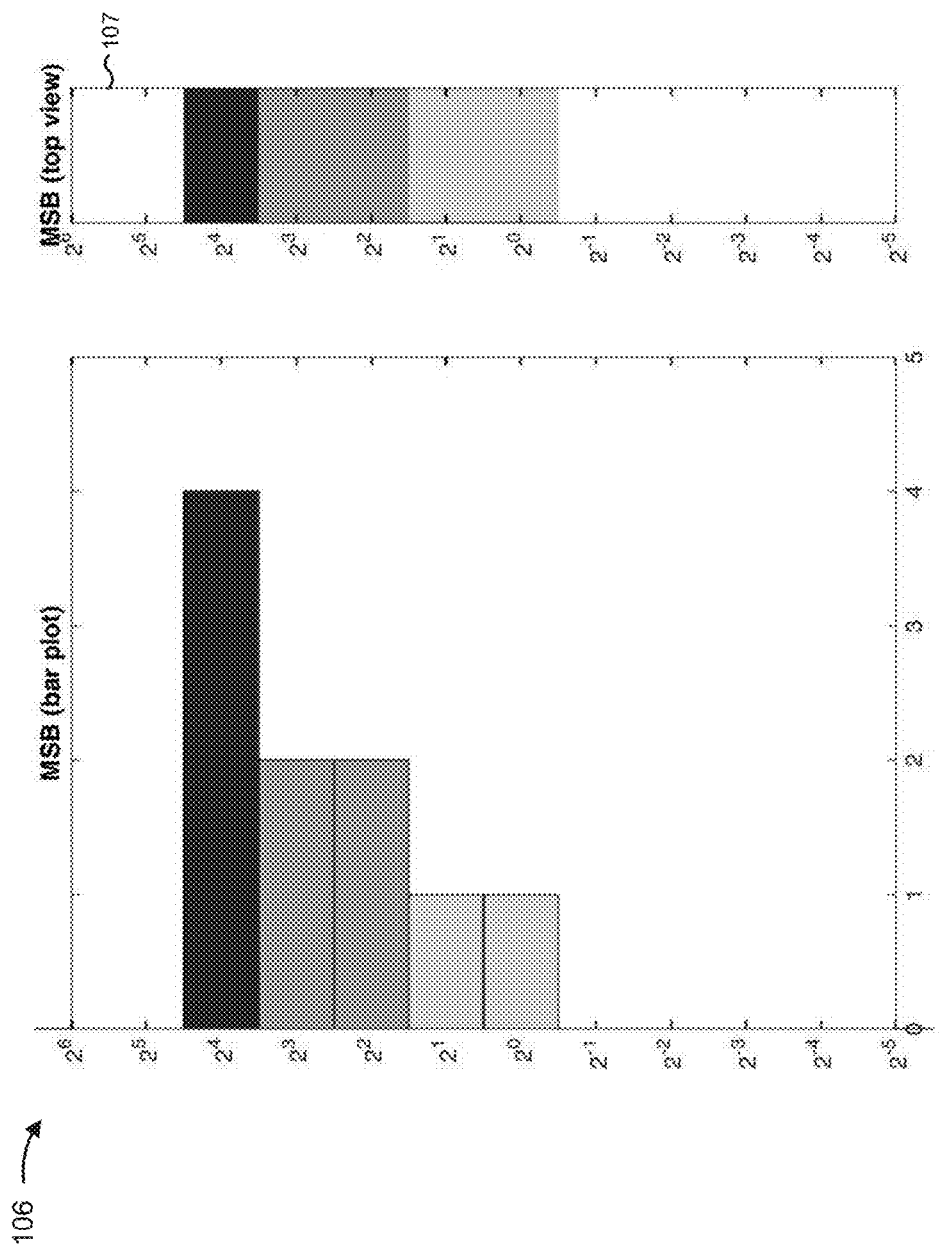
Figure 1F:
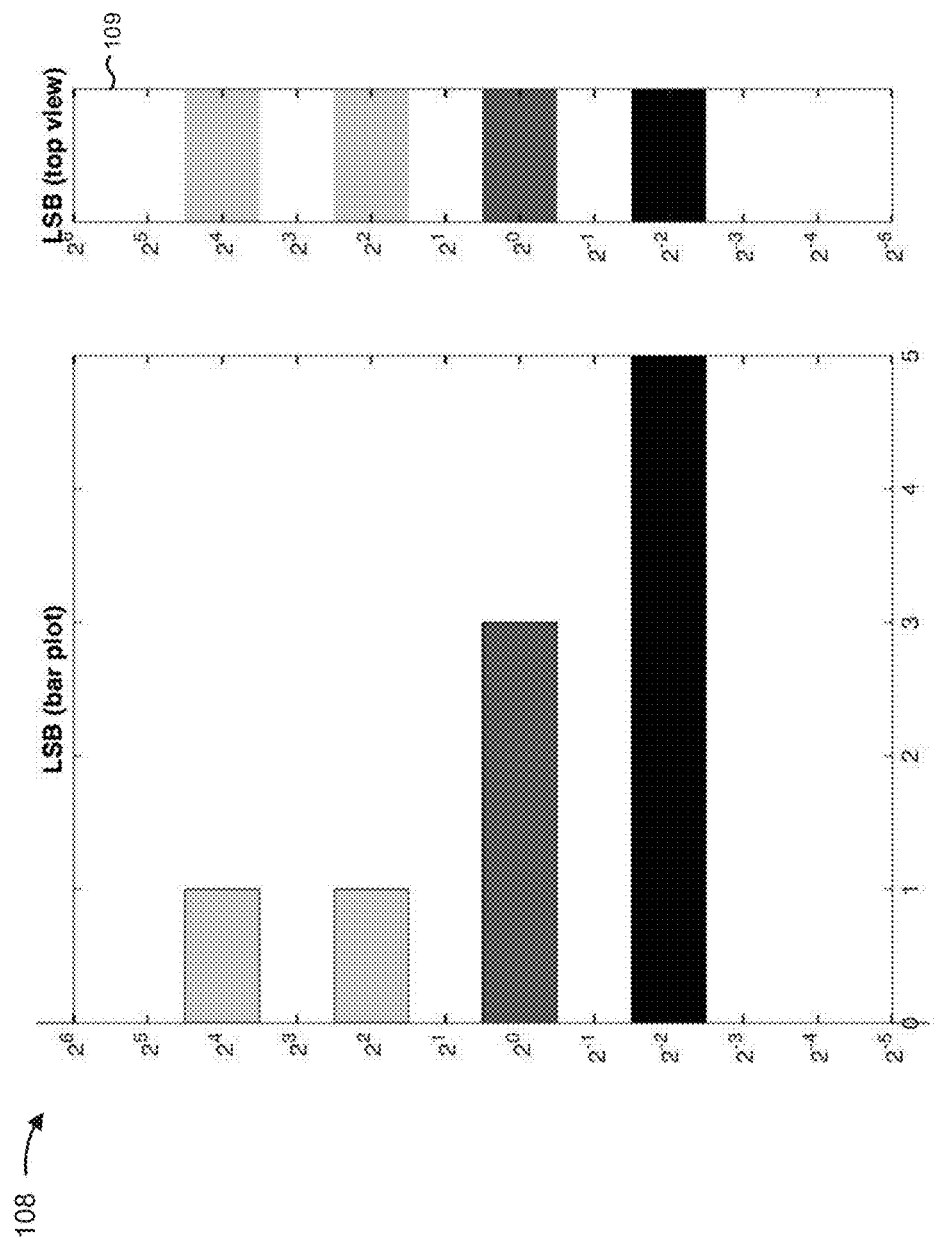
Figure 1G:
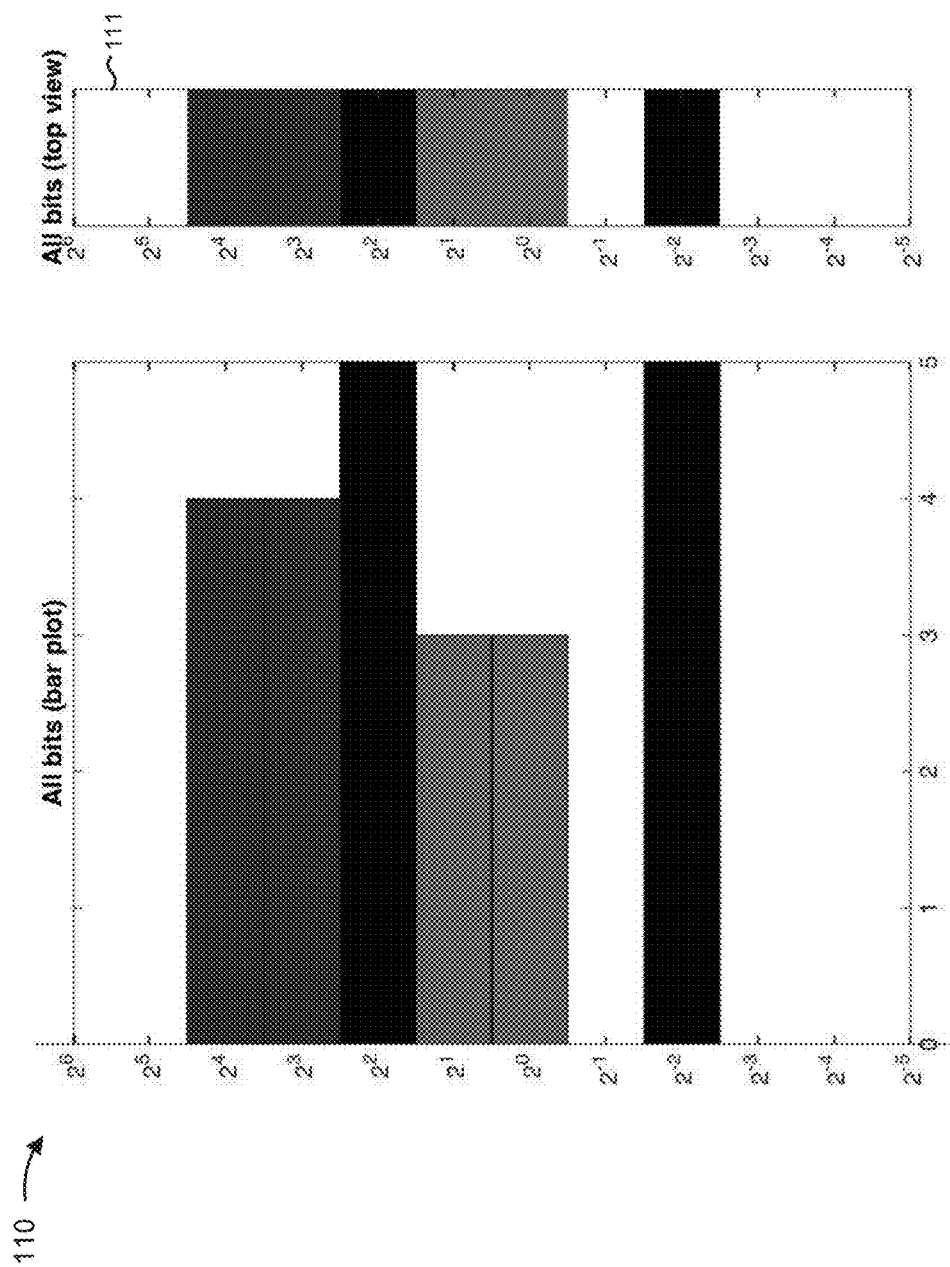

FIGS. 1E-1G show example bar graphs 106, 108, 110 plotting the data from table 104. Bar graph 106 shows counts of the digits that were used as most significant digits for the values represented by the variable y. A top view graph 107 compresses the information shown in bar graph 106 by color coding magnitudes of the counts of the digits used. Similarly, bar graph 108 shows counts of the digits that were used as least significant digits for the values represented by the variable y. A top view graph 109 that shows the information from bar graph 108. Bar graph 110 shows counts of all the significant digits that were used for the values represented by the variable y. A top view graph 111 that shows the information from bar graph 110.

Referring back to FIGS. 1A and 1B, each histogram may be a top view graph, such as top view graph 107, that shows information about significant digits used for values for each variable. A plurality of such graphs for different variables may be aggregated to generate a visualization.

The significant digits that are used for values of the variable may be shaded using different colors to represent different quantities of times that a significant digit was used by a variable to represent a value. As shown in example implementation 100, the range may be represented as powers of two where each power of two may correspond to a significant digit (in binary) used to represent a value. Thus, significant digits above 0 represent whole portions of a number, while significant digits below zero represent fractional portions of a number.

For example, a column in example implementation 100 is highlighted by darkened vertical bars and an icon consisting of pointing finger. The highlighted column may show the range of an expression "acc+b(j)*z(k)" as highlighted in a code section of example implementation 100. The darkened portions of the column may show the portions of the range (e.g., the most significant digits) that are used by the expression "acc+b(j)*z(k)" to represent values of the expression. As shown, the darkened portion is darker at the top, corresponding to significant digits closer to 1 (e.g., corresponding to 0 on the log 2 scale shown on the axis) and gradually lightens further down the column, which may indicate that values stored by the expression "acc+b(j)*z(k)" more often use higher-order significant digits (e.g., more significant fractional bits) than lower-order significant digits (e.g., less significant fractional bits).

A visualization may include multiple histograms corresponding to different variables, which may allow the user to easily see the ranges of variables and expressions across large portions of code, such as an entire project. The visualizations may be manipulated to display certain types of variables or expressions and/or certain portions of the code. The visualizations may also be sorted to show variables with similar ranges. The visualizations may also include data type information, allowing the user to determine overflows or underflows of values for assigned data types. The visualization may also provide inputs so that the user may modify the underlying code using the visualization. For example, data types may be assigned or modified using the visualization. The visualization may also include links from each column to corresponding sections of code for each of the variables and expressions. Thus, the user may be able to receive information about multiple variables and expressions across portions or entireties of code. The user may also be provided interfaces through which the code may be modified.

Figure 1H:
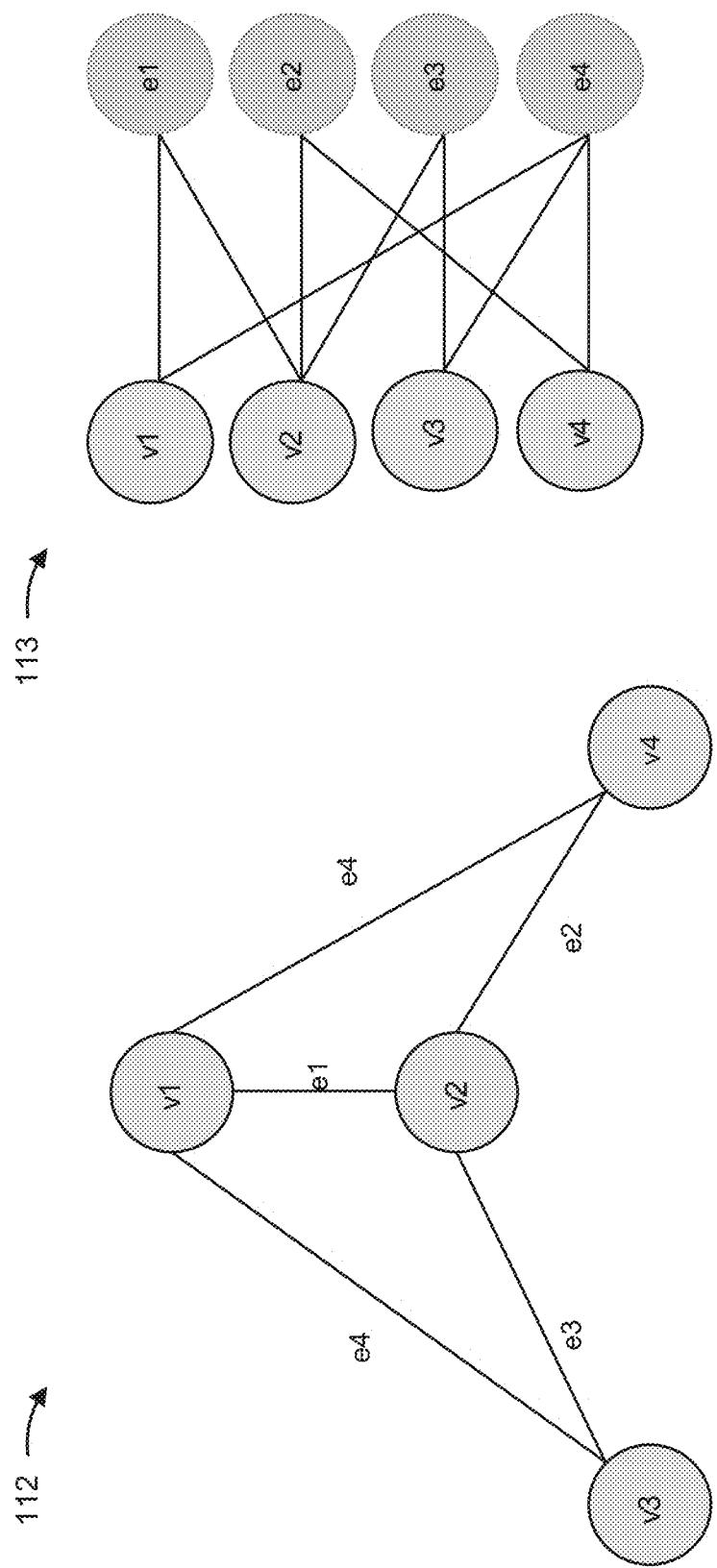

The visualizations may also include relationship information, allowing the user to determine relationships between different entities. Entities may include variables, expressions, functions, etc. For example, FIG. 1H shows example relationship diagrams 112, 113 displaying relationships between different variables and expressions. Relationship diagram 112 shows variables as nodes, connected by expressions as edges. Relationship diagram 113 shows variables and expressions as nodes, connected based on relationships between the variables and expressions. Other diagrams may be used to depict such relationship information. The relationship information may be used to provide additional information to the user for assigning data types. The relationship information diagrams may also be associated with histograms or other graphs. For example, the user may click on portions of a bar graph, such as graph 100, and be shown diagrams of relationship information for variables and/or expressions associated with the portions of the graph. Alternatively, or additionally, the user may click on portions of a relationship information diagram, such as relationship diagram 113, and be shown relevant portions of a bar graph or portions of the bar graph may be highlighted and/or sorted that display associated variables and/or expressions. The user may navigate (e.g., scroll, click and drag) through the bar graph and/or the relationship information diagram and be shown relevant portions of the other.

Figure 1I:
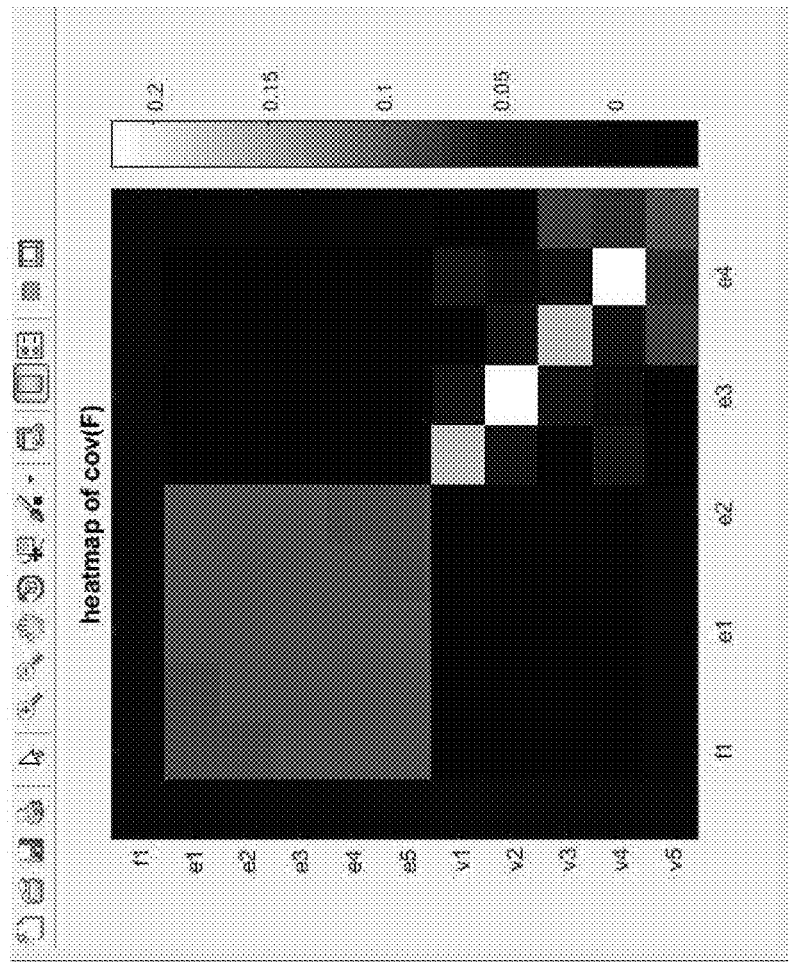

FIG. 1I shows another example relationship diagram 114 depicting relationship information. Relationship diagram 114 is a heat map that shows degrees of covariance between variables, expressions, and functions. The darker portions may show variables, expressions, and functions that are less correlated, while the lighter portions may show variables, expressions, and functions that are more correlated. Variables, expressions, and functions that are more correlated may have a greater impact on each other if changes are made to one. For example, from the heat map, a data type may be changed for a variable, v2, which may have a greater impact on expressions e3 and e4 than on expression e1. The user may use such information to help determine more efficient data type assignments for variables. The information may also provide the user a heuristic-based narrowing of a search space for inefficient assignment of data types for variables. Assigning efficient data types for variables allows the computer to more efficiently use resources such as memory and computational power. Visualizations may also be used to customize constraints of data type assignments. For example, the user may select one or more variables and constrain the selected variables to a specific data type and allow a client device to automatically optimize remaining unconstrained variables.

Figure 1J:
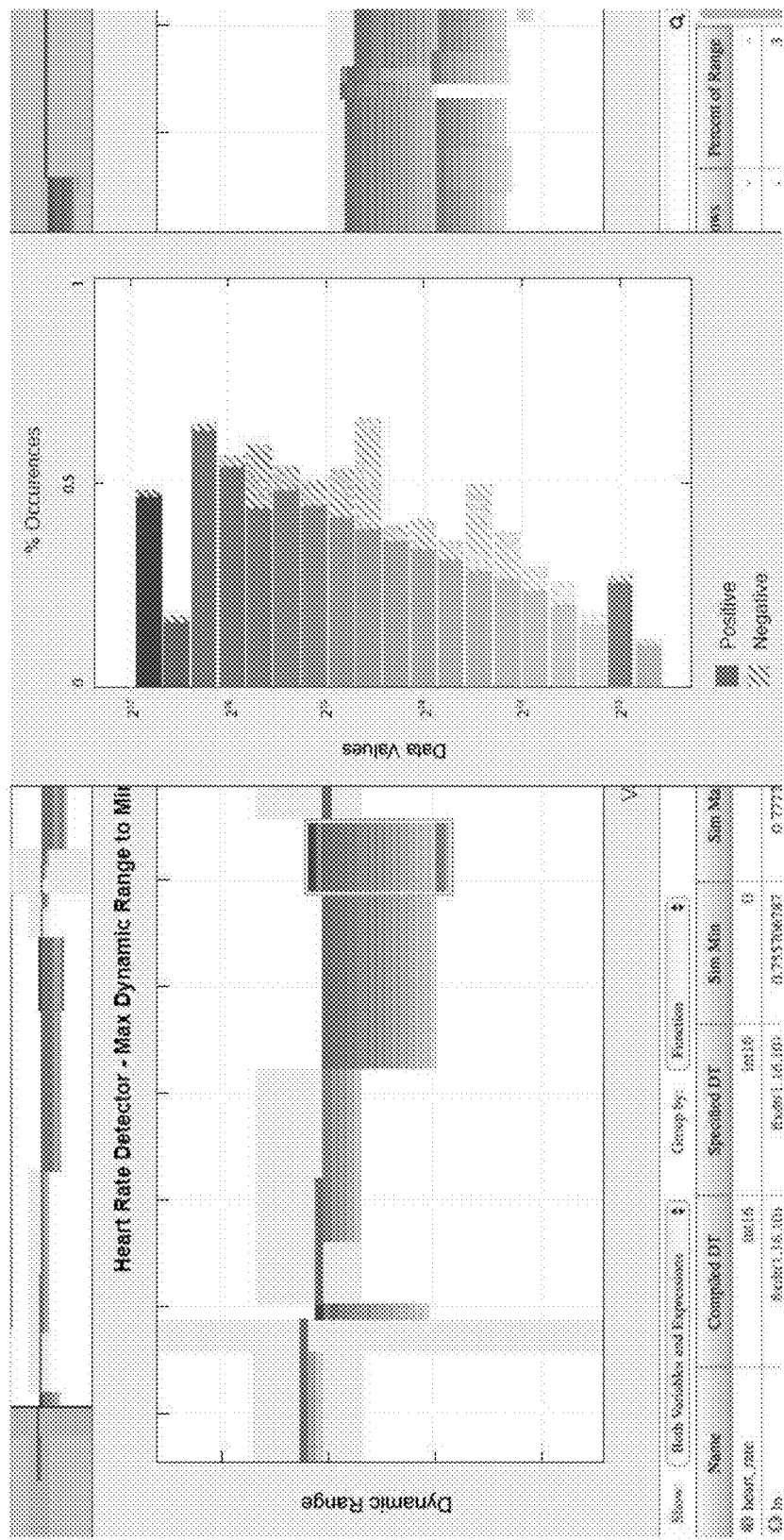

FIG. 1J shows another example visualization 116. Visualization 116 may include histograms corresponding to multiple entities and represent ranges of the entities. In some implementations, histograms may provide additional information (e.g., using shading or other distinctions) by showing more than one type of range (e.g., a derived range, a designed range, a simulated range, a proposed range, a positive value range, a negative value range, etc.) or other information. In some implementations, a group of histograms may be further collapsed into a single histogram. For example, the user may select a group of histograms of entities that are more correlated and collapse the group of histograms into one or more histograms, as the visualization may indicate that the group of histograms would be affected similarly to one another. In some implementations, histograms may provide time-based information. For example, histograms may collapse values of variables over a given time interval in execution of code (and/or a model). Such histograms may be expanded to show users a time interval in which an overflow first occurs. The time intervals may be specified by the user and/or may include default settings of various lengths or proportions. For example, the user may request histograms of values of a variable for every five seconds of execution time. The visualization may provide one histogram for each of the five second intervals that collapses values of the variables for each of the intervals. The visualization may allow the user to interact with each of the histograms to further expand and/or collapse the histograms into smaller or larger time intervals. The visualization may also include a slider or other interface that allows the user to vary the lengths of the time intervals. The time intervals may also vary and/or include specified portions of the execution of the code and/or model.

As indicated above, FIGS. 1A-1J are provided as an example. Other examples are possible and may differ from what was described in connection with FIGS. 1A-1J.

Figure 2:
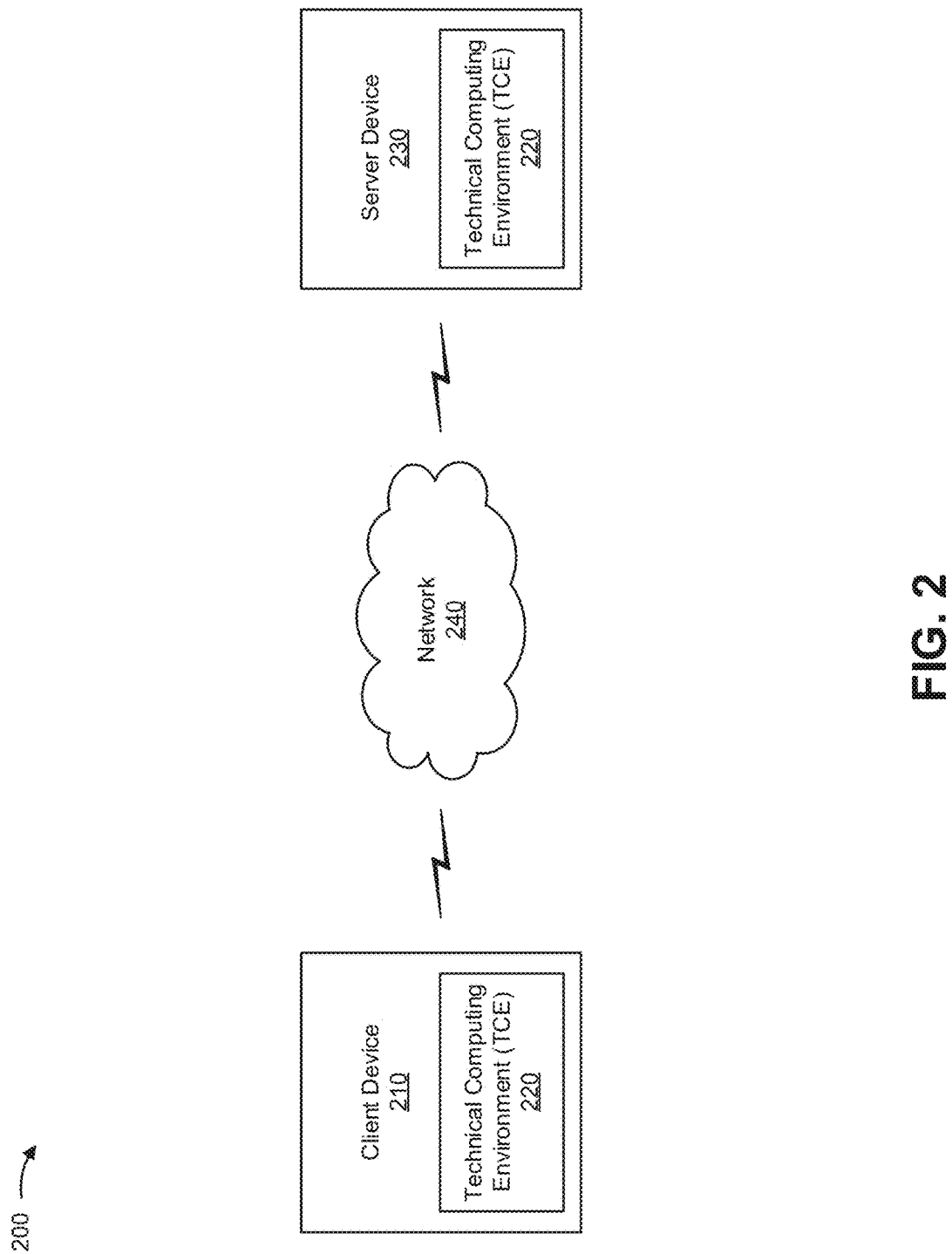
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a client device 210, which may include a technical computing environment (TCE) 220. Furthermore, environment 200 may include a server device 230, which may include TCE 220, and a network 240. Devices of environment 200 may interconnect via wired connections, wireless connections, or a combination of wired and wireless connections.

Client device 210 may include one or more devices capable of receiving, generating, storing, processing, and/or providing code and/or information associated with code (e.g., a visualization generated based on code). For example, client device 210 may include a computing device, such as a desktop computer, a laptop computer, a tablet computer, a mobile phone (e.g., a smart phone, a radiotelephone, etc.), or a similar device. Client device 210 may provide visualizations and/or representations of data. In some implementations, client device 210 may receive information from and/or transmit information to server device 230.

Client device 210 may host TCE 220. TCE 220 may include any hardware-based component or a combination of hardware and software-based components that provides a computing environment that allows tasks to be performed (e.g., by users) related to disciplines, such as, but not limited to, mathematics, science, engineering, medicine, and business. TCE 220 may include a text-based environment (e.g., MATLAB® software by The MathWorks, Inc.), a graphically-based environment (e.g., Simulink® software, Stateflow® software, SimEvents® software, etc., by The MathWorks, Inc.; VisSim by Visual Solutions; LabView® by National Instruments; Agilent VEE by Agilent Technologies; Advanced Design System (ADS) by Agilent Technologies; Agilent Ptolemy by Agilent Technologies; etc.), or another type of environment, such as a hybrid environment that may include, for example, a text-based environment and a graphically-based environment.

TCE 220 may include, for example, a user interface that provides visualizations of data, such as dynamic ranges of variables and/or expressions of code. A user interface may also provide a code editor, which may be used to view and/or edit code and may be used generate visualizations and/or linked to visualizations.

Server device 230 may include one or more devices capable of receiving, generating, storing, processing, and/or providing code and/or information associated with code. For example, server device 230 may include a computing device, such as a server, a desktop computer, a laptop computer, a tablet computer, or a similar device. In some implementations, server device 230 may host TCE 220. In some implementations, client device 210 may be used to access one or more TCEs 220 running on one or more server devices 230. For example, multiple server devices 230 may be used to execute code (e.g., serially or in parallel), and may provide respective results of executing the code to client device 210.

In some implementations, client device 210 and server device 230 may be owned by different entities. For example, an end user may own client device 210, and a third party may own server device 230. In some implementations, server device 230 may include a device operating in a cloud computing environment. In this way, front-end applications (e.g., a user interface) may be separated from back-end applications (e.g., code execution).

Network 240 may include one or more wired and/or wireless networks. For example, network 240 may include a cellular network, a public land mobile network (PLMN), a local area network (LAN), a wide area network (WAN), a metropolitan area network (MAN), a telephone network (e.g., the Public Switched Telephone Network (PSTN)), an ad hoc network, an intranet, the Internet, a fiber optic-based network, a private network, a cloud computing network, and/or a combination of these or other types of networks.

The number and arrangement of devices and networks shown in FIG. 2 is provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
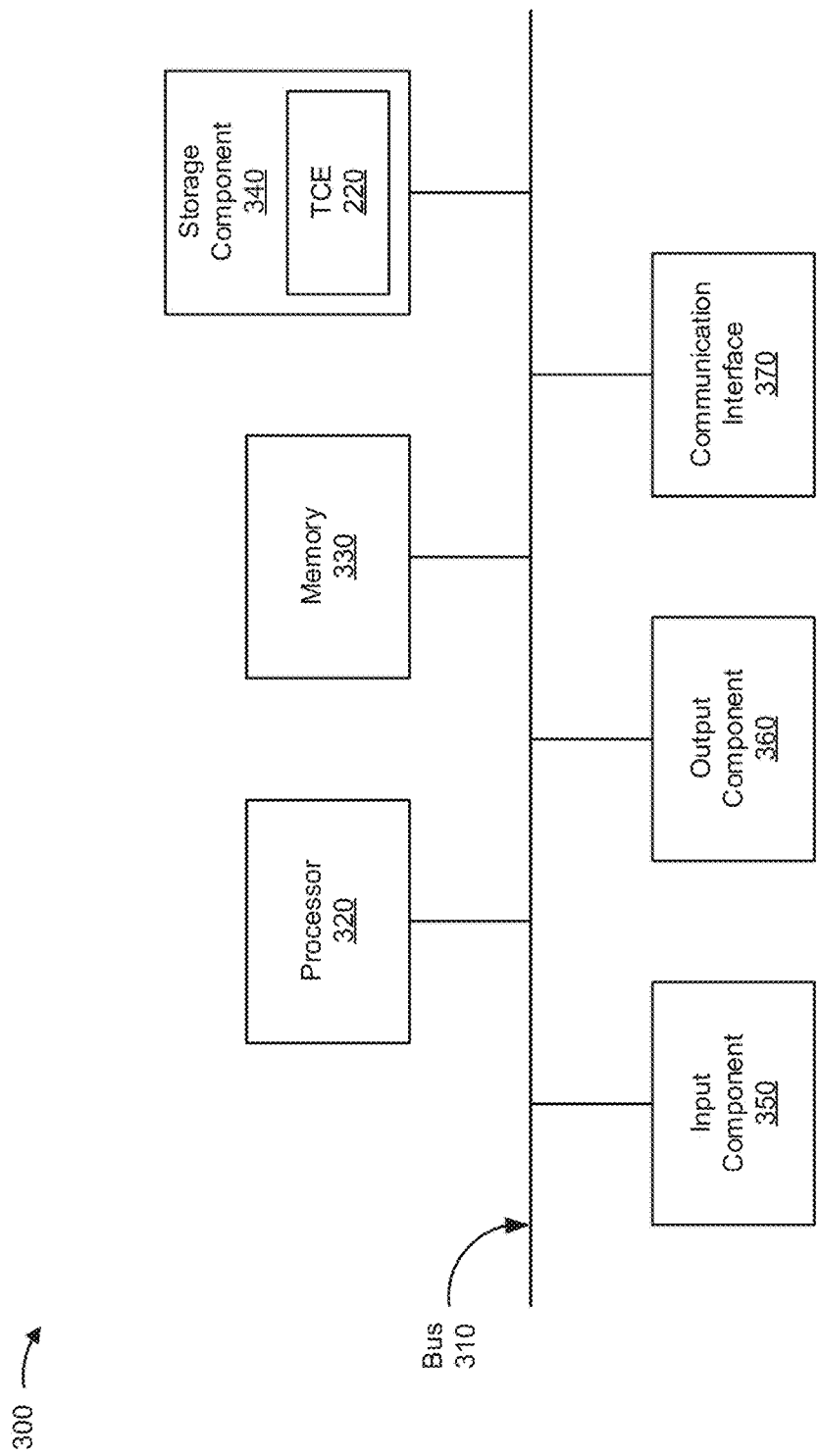
FIG. 3 is a diagram of example components of one or more devices of FIG. 2.

FIG. 3 is a diagram of example components of a device 300. Device 300 may correspond to client device 210 and/or server device 230. In some implementations, client device 210 and/or server device 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 takes the form of a central processing unit (CPU), a graphics processing unit (GPU), an accelerated processing unit (APU), etc.), a microprocessor, a field-programmable gate array (FPGA), an application-specific integrated circuit (ASIC), or another type of processing componenet that interprets and/or executes instructions, and/or that is designed to implement one or more computing tasks. In some implementations, processor 320 may include multiple processor cores for parallel computing. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive. In some implementations, storage component 340 may store TCE 220.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 is provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4A:
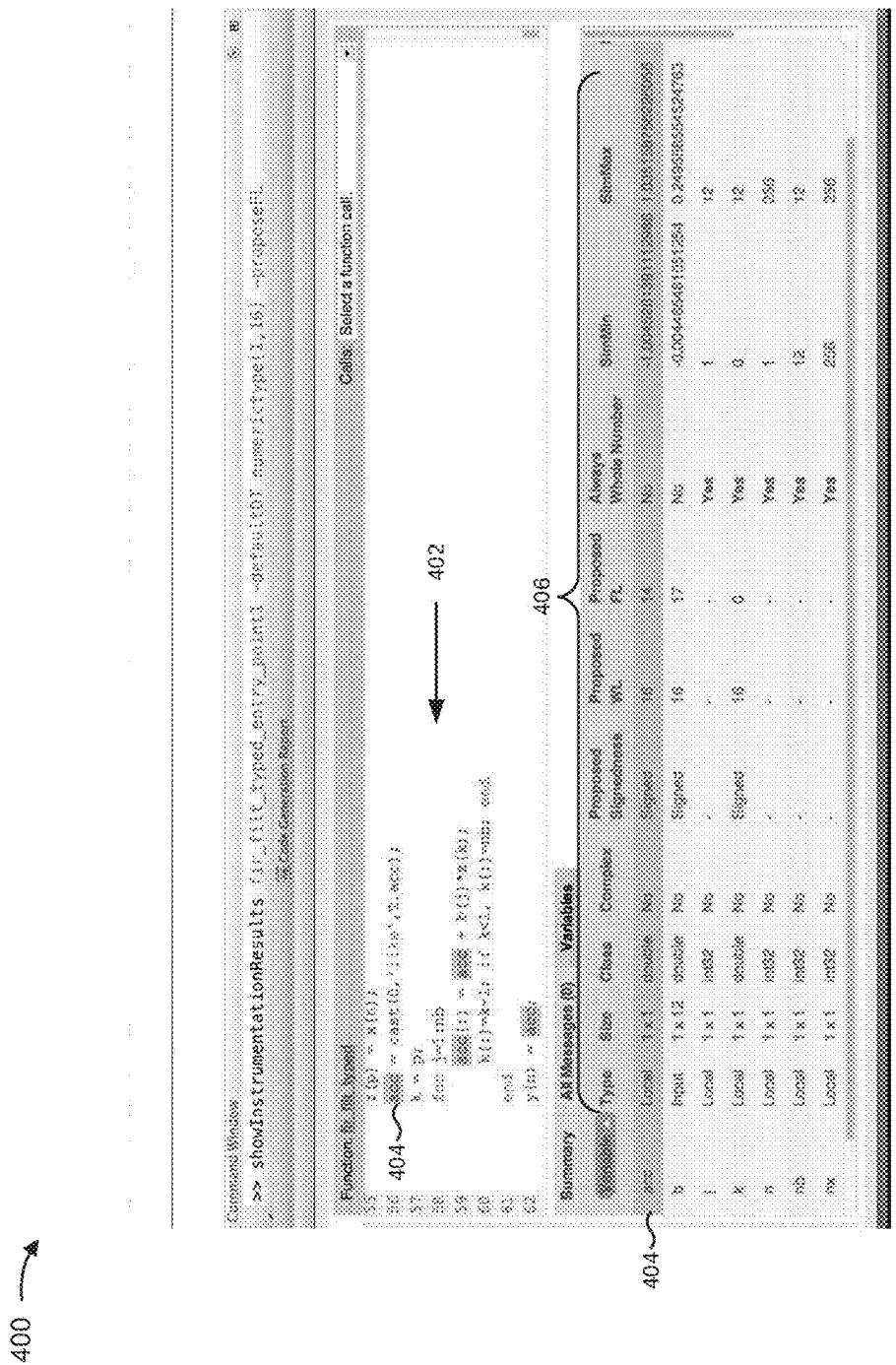
FIG. 4A is a diagram of an example data set for generating a visualization of data types.
Figure 4B:
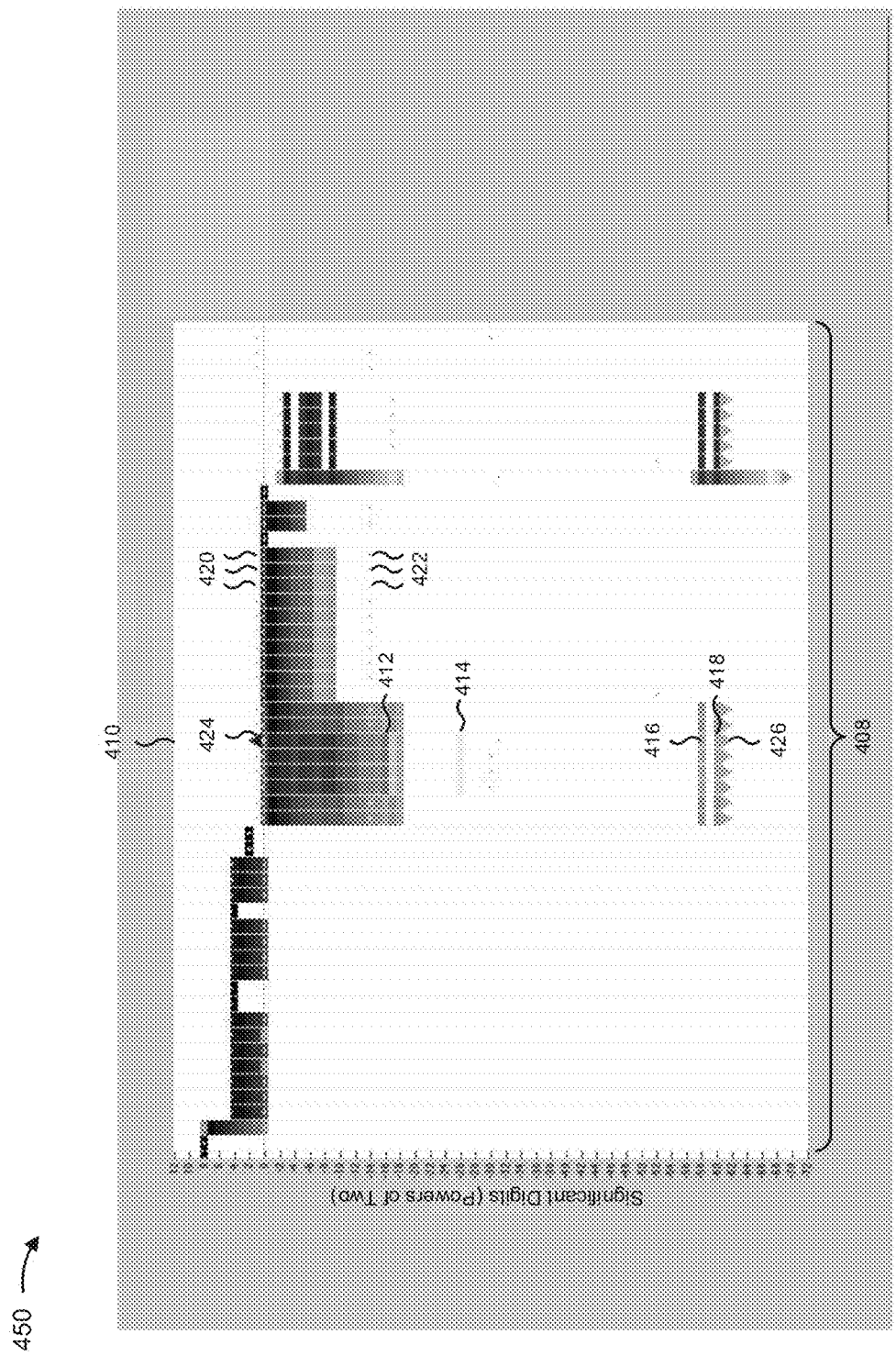
FIG. 4B is a diagram of an example implementation of a visualization of data types.

FIGS. 4A and 4B are diagrams of an example implementations 400, 450 for generating a visualization of data types. As shown in FIG. 4A, a code portion 402 may include variables, such as "acc" 404. The variables may represent values as code portion 402 is executed (e.g., using a simulation such as a set of test cases on the code). Information associated with each variable may be obtained through static analysis of code portion 402 (e.g., prior to executing code portion 402) and/or analysis of code portion 402 during execution. As further shown in FIG. 4A, information associated with each variable may include characteristics 406 such as an assigned data type, a proposed signedness (e.g., signed or unsigned), a proposed word length (e.g., a number of bits assigned to the variable), a simulated minimum, and a simulated maximum.

For example, variable "acc" 404 is shown as having an assigned data type of "double," a proposed signedness of "signed," a proposed word length of "16," a simulated minimum of "−1.0045281391112986" and a simulated maximum of "1.035158756226056." In addition to simulated minimum and simulated maximum, the dynamic range of variable "acc" 404 may also be determined. For example, during simulation, a quantity for each of the most significant digits used by each of the values represented by "acc" 404 may be totaled to determine the dynamic range of the significant digits.

Information associated with each variable may be used to generate a visualization, such as the example implementation 450 of FIG. 4B. As shown in FIG. 4B, each column 408 may represent a variable (or an expression including one or more variables) of code. Each column 408 may include one or more shaded portions indicating a range of values represented by the variable. Each column 408 may also include other indicators, such as a range of an assigned data type of each variable, an overflow indicator, an underflow indicator, and/or other indicators of information associated with each variable.

For example, column 410 may represent variable "acc" 404 from FIG. 4A. As shown, column 410 has a first shaded portion 412, a second shaded portion 414, a third shaded portion 416, and a fourth shaded portion 418, each indicating ranges of values represented by variable "acc" 404 during simulation of the code. A top of first shaded portion 412 starts at 0 (which corresponds to $2^0$) and a remainder of first shaded portion 412 extends below 0, which may indicate that the values represented by "acc" 404 are fractional values. For example, significant digits below 0 represent values of 2 raised to a power of a negative number. As there are no shaded portions above 0 for column 410, the values represented by "acc" 404 in the example simulation may be numbers containing only fractional parts (e.g., numbers between −1 and 1, exclusive).

In the example of FIG. 4B, first shaded portion 412 is darker at the top and generally gets lighter at the bottom. This shading pattern may indicate that the values represented by "acc" 404 more often use higher-order significant digits than lower-order significant digits. For example, darker areas can indicate higher incidences of values as compared to lighter areas which can indicate fewer incidences of values. Second, third, and fourth shaded portions 414, 416, and 418 may indicate various other significant digits used by values represented by "acc" 404. As the second, third, and fourth shaded portions 414, 416, 418 are each below first shaded potion 412, the lower shaded portions indicate use of less significant digits by the values represented by the variable. The gaps between the shaded portions may indicate more narrow ranges within the range of values represented by "acc" 404, as some significant digits are not used by any of the values represented by "acc" 404.

In some implementations, a range (e.g., a representable range and/or a dynamic range and/or a precision) of a data type assigned to a variable may be represented in the visualization. For example, a dot or other indicator may show an upper and lower bound of a range of an assigned data type. An indicator 420 may show the upper bound of a range of an assigned data type for each of the columns (e.g., variables). Another indicator 422 may show the lower bound of the range of the assigned data type for each of the columns. As shown, indicator 420 and indicator 422 are similar in appearance. In other implementations, indicator 420 and indicator 422 may have differences in appearance, such as a different color, shape, size, etc.

In some implementations, overflow and/or underflow information may be represented in the visualization. For example, if a magnitude of values represented by a variable in a simulation exceeds an upper bound of a range of a data type assigned to the variable, an overflow condition may occur. For example, a variable may be unable to accurately represent a value if a variable is assigned too few bits for storing a value with a large magnitude. In such a case, as in column 410, the shaded portion, in this case first shaded portion 412, may exceed an upper bound indicator. In addition, the visualization may include an overflow indicator 424, such as an arrow at the top of first shaded portion 412.

Similarly, an underflow condition may occur if a magnitude of a value represented by a variable is too small for a variable to accurately represent with a range of a data type assigned to the variable. Again referring to column 410, third shaded portion 416 and fourth shaded portion 418 are positioned below a lower bound indicator 422 for column 410. Thus, an underflow condition may be occurring with variable "acc" 404 as some of the values represented by "acc" 404 require more bits than currently assigned by the data type to be accurately represented. The visualization may indicate the underflow condition with an underflow indicator 426, such as an arrow extending below fourth shaded portion 418.

As indicated above, FIGS. 4A and 4B are provided merely as an example. Other examples are possible and may differ from what was described with regard to FIGS. 4A and 4B. For example, indicators such as the upper and lower bound indicators and overflow and underflow indicators may be presented differently than shown in the examples. Further, other indicators may be used to provide additional or different information associated with each variable, such as a maximum value represented by a variable, a machine epsilon value for a variable, etc. In some implementations, the indicators may be toggled on and off, e.g., via a received input, to show and hide some or all of the indicators. Alternatively, or additionally, the range of values for each variable may be presented differently. For example, the range of values for each variable may be presented as a heat map or a color chart rather than a histogram. Further, while the histograms use shading in FIGS. 4A and 4B, other techniques for indicating range can be used such as borders, fill patterns, icons, labels, etc.

In some implementations, variables and/or expressions may be grouped so that each column represents more than one variable, such as a function or other portion of code. In some implementations, the visualization may allow a user to collapse and expand columns to represent different numbers of variables. Such collapsing and expanding of columns may be nested to provide a hierarchy of variables, such as variables contained in a function, which are in turn nested in a project file. Other such hierarchies and/or relations may be used to group variables for visualization.

Figure 5A:
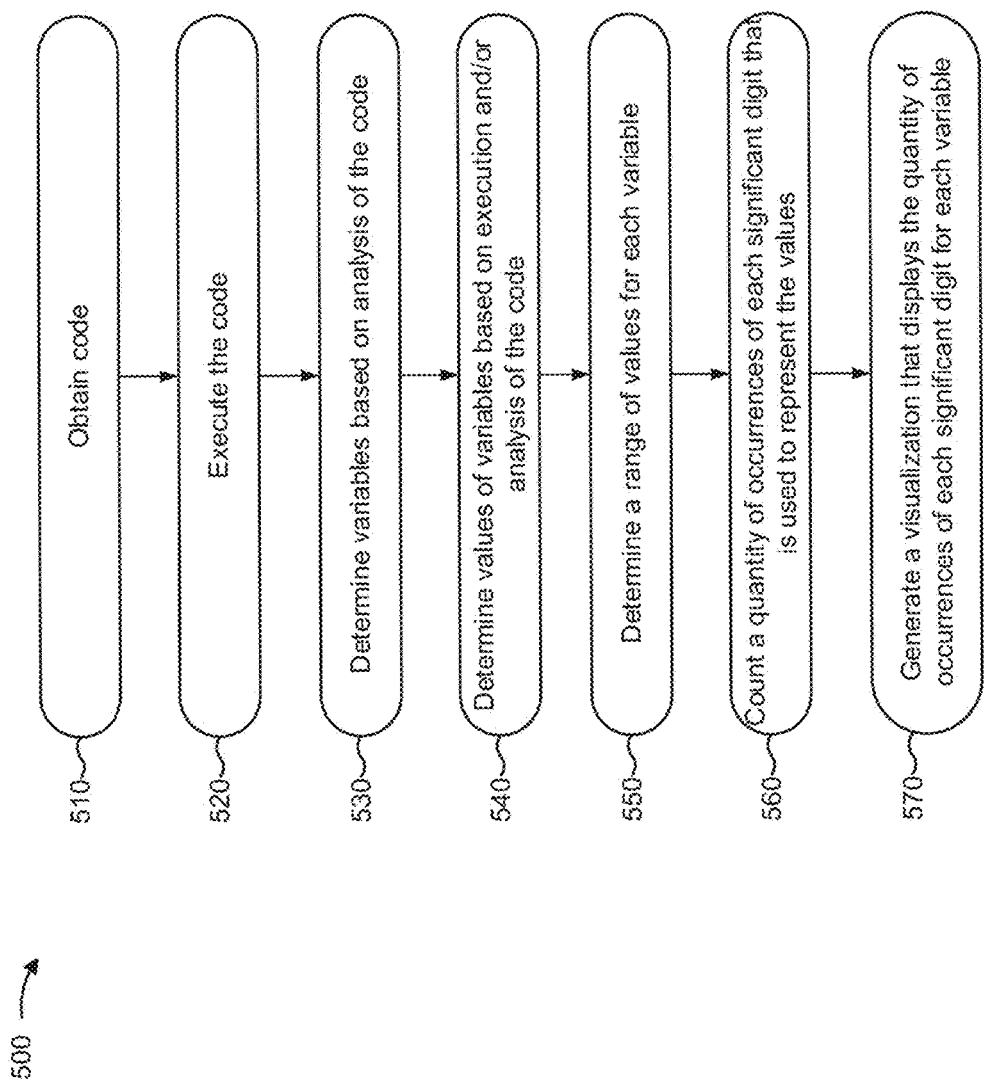
FIGS. 5A and 5B are flow charts of example processes for generating a visualization of data types.

FIG. 5A is a flow chart of an example process 500 for generating a visualization of data types. In some implementations, one or more process blocks of FIG. 5A may be performed by client device 210. In some implementations, one or more process blocks of FIG. 5A may be performed by another device or a group of devices separate from or including client device 210, such as server device 230.

As shown in FIG. 5A, process 500 may include obtaining code (block 510), and executing the code (block 520). For example, a user may write code using client device 210 or client device 210 may receive code to be analyzed (e.g., from a file system, a remote device, etc.). Client device 210 may execute the code, such as by executing a set of test cases on the code in a testing environment or by executing the code multiple times in a simulation environment. In some embodiments, the code may include different versions of a portion of code. Alternatively, or additionally, client device 210 may execute the code in a production environment rather than in a testing environment.

In some embodiments, client device 210 may execute the code using data types different from the data types assigned to some or all of the variables. For example, a particular variable may be assigned an integer data type. Client device 210 may execute the code using a double precision data type for the particular variable. Using a different data type may provide additional information, such as overflow and underflow information. For example, executing the code using the integer data type for the particular variable may result in only integer values being stored in the particular variable, even though non-integer values may be assigned to the particular variable.

As further shown in FIG. 5A, process 500 may include determining variables based on analysis of the code (block 530). For example, client device 210 may determine variables in all or a portion of the code through a static analysis of the code (e.g., by analyzing a syntax of the code) or deriving ranges based on the syntax of the code. Alternatively, or additionally, variables may be determined during execution of the code. In some implementations, client device 210 may also determine expressions, which may include one or more variables in the code.

In some embodiments, client device 210 may analyze the code using data types different from the data types assigned to some or all of the variables. Such a process may be similar to the process described above with regard to executing the code using different data types from those assigned to the variables.

As further shown in FIG. 5A, process 500 may include determining values of variables based on execution and/or analysis of the code (block 540), and determining a range of values for each variable (block 550). For example, client device 210 may determine, for each variable, different values represented by the variable throughout an execution simulation of the code. Based on the values that are represented by the variable, client device 210 may determine a range of the values for the variable, including information such as a representable range of the variable and a dynamic range of the variable. As described above, the range of the values for the variable may be based on positions of significant digits used by the values, such as most significant digits, least significant digits, and/or all significant digits. The dynamic range may be determined by the highest-order and lowest-order significant digits used by the values represented by the variable. Client device 210 may determine the ranges for variables (and/or expressions) in a portion or entirety of the code. In some embodiments, based on the values that are represented by the variable, client device 210 may determine additional, or alternative, characteristics of the variables. For example, client device 210 may determine a precision of the variables, a slope and bias of the variables, and other such characteristics of the variables.

As further shown in FIG. 5A, process 500 may include counting a quantity of occurrences of each significant digit, in the range, that is used to represent the values (block 560). For example, client device 210 may store a count for each significant digit used by a variable to store a value represented by each variable. As a value is represented by the variable, client device 210 may increment the count for the significant digits that is the most significant digit used by the value represented by the variable. In some embodiments, client device 210 may increment the count for each significant digit that is the least significant digit used by each value represented by the variable. In some embodiments, client device 210 may increment the count for the all the significant digits used by the values represented by the variable.

As further shown in FIG. 5A, process 500 may include generating a visualization that displays the quantity of occurrences of each significant digit in the range for each variable (block 570). For example, as described above in FIG. 4B, client device 210 may generate a visualization that includes histograms for each variable. The histograms may be shaded darker to show greater quantities of occurrences of significant digits from the values represented by the variable. Each variable may be presented in a separate column.

Although FIG. 5A shows example blocks of process 500, in some implementations, process 500 may include additional blocks, fewer blocks, different blocks, or differently arranged blocks than those depicted in FIG. 5A. Additionally, or alternatively, two or more of the blocks of process 500 may be performed in parallel.

Figure 5B:
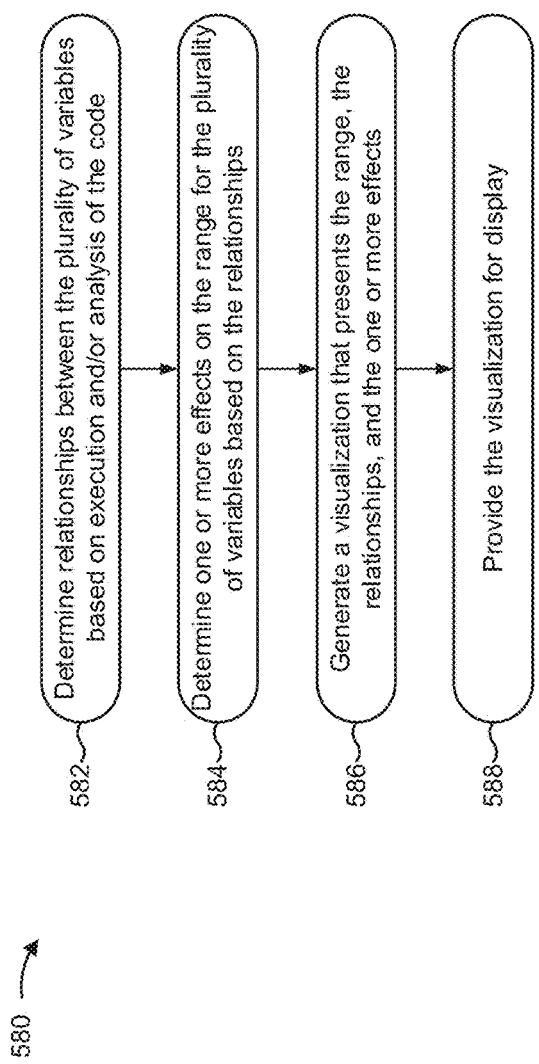

FIG. 5B is a flow chart of an example process 580 for generating a visualization of data types. In some implementations, one or more process blocks of FIG. 5B may be performed by client device 210. In some implementations, one or more process blocks of FIG. 5B may be performed by another device or a group of devices separate from or including client device 210, such as server device 230.

In some implementations, one or more process blocks of FIG. 5B may be performed in conjunction with one or more process blocks of example process 500 of FIG. 5A. For example, in some implementations process 580 may include one or more of obtaining code, executing the code and/or analyzing the code, determining values of variables based on execution and/or analysis of the code, and/or determining a range of values for each variable.

As shown in FIG. 5B, process 580 may include determining relationships between the variables based on executing the code and/or analyzing the code (block 582). For example, client device 210 may determine degrees of correlation between the variables. Client device 210 may also determine degrees of correlation between entities, which may include variables, expressions, and/or functions. In some embodiments, client device 210 may determine degrees of correlation by generating one or more intermediate representations (IRs) and analyzing the one or more IRs. For example, client device 210 may execute and/or analyze the code and assign identifications to each entity (e.g., variables, expressions, functions, etc.). Client device 210 may analyze compiled code paths and generate a node tree (or other graphical representation) that depicts relationships between the entities.

As shown in FIG. 5B, process 580 may include determining one or more effects on the range for the variables based on the relationships between the variables (block 584). For example, client device 210 may determine based on the node tree how a change in one entity may affect other entities. For example, the node tree may provide information to the user based on how closely connected two or more entities are in the node tree. The node tree may also provide information depending on the types of entities that are connected in the node tree. For example, an edge from a variable to an expression may represent an assignment or an operation in the corresponding code. An edge from an expression to a function may represent a function call. An edge from a variable to another variable may represent an operation. An edge from a function to another function may show control flow. The node tree may include additional information about the nodes, such as entity type, assigned data types, etc. This additional information may help the user determine more quickly the source of overflows or other inefficient data type assignments.

As shown in FIG. 5B, process 580 may include generating a visualization that presents the range, the relationships, and the one or more effects (block 586). For example, client device 210 may include the node tree (and/or other graphical representation, such as relationship diagram 114 of FIG. 1I) depicting the relationships along with histograms for each variable (and/or entities). Client device 210 may receive interactions with the visualization and provide updated visualizations accordingly. For example, the user may select one or more histograms for one or more entities. In response, client device 210 may update the visualization to show the corresponding entities in the node tree. For example, client device 210 may show a highlighted portion of the node tree, a zoomed in portion of the node tree, or otherwise distinguish a portion of the node tree corresponding to the one or more selected histograms. Conversely, the user may interact with the node tree and client device 210 may update the histograms to distinguish entities corresponding to the selected nodes. For example, the user may select one or more nodes, zoom in to a portion of the node tree, scroll through the node tree, request certain types of entities to be shown, select different levels of hierarchy or granularity of the node tree, etc. The node tree may also depict additional relationship information between the entities. For example, a selected node may be distinguished in one way while other nodes that are more correlated to the selected node may be distinguished in a second way. Similar information may be provided in the histograms.

Figure 5C:
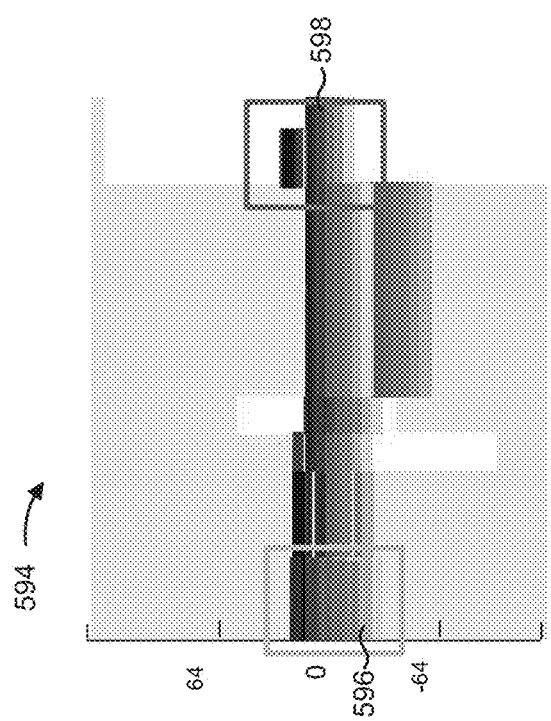
FIG. 5C is a diagram of an example implementation for interacting with a visualization of data types.
Figure 5C:
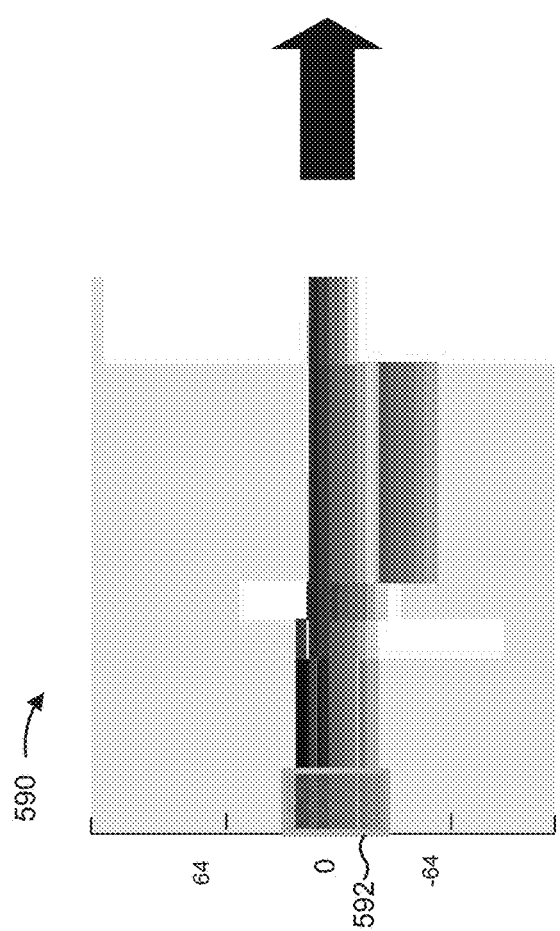

Client device 210 may also provide mechanisms for the user to change data types through interacting with the visualization, as will be further discussed in detail below. Client device 210 may update the visualization to show the effects of such changes on other entities. For example, FIG. 5C shows an example user interaction with a visualization 590. The user may select a group of entities, shown by a green highlighted box 592. The user may change data types of the selected group of entities. Client device 210 may generate an updated visualization 594 that shows the selected group of entities with the changed data type (shown in a green box 596). The updated visualization 594 may also distinguish entities that are affected by the changed data type, for example, in a red box 598. Client device 210 may determine which entities are affected based on the relationships between the entities. While this example shows colored boxes and highlights, other techniques may be used to distinguish entities.

As shown in FIG. 5B, process 580 may include providing the visualization for display (block 588). In some embodiments, client device 210 may provide portions of the visualization for display (e.g., a histogram, a relationship diagram, etc.). Other visualization displays are further described below.

Although FIG. 5B shows example blocks of process 580, in some implementations, process 580 may include additional blocks, fewer blocks, different blocks, or differently arranged blocks than those depicted in FIG. 5B. Additionally, or alternatively, two or more of the blocks of process 580 may be performed in parallel.

FIGS. 6A-6F are diagrams of an example implementation 600 for interacting with a data type visualization. As described above, each column 602 of the visualization may represent a variable (and/or an expression). In some embodiments, variables may represent data types associated with code executing on a plurality of processing devices, such as processors in a distributed computing environment.

Figure 6A:
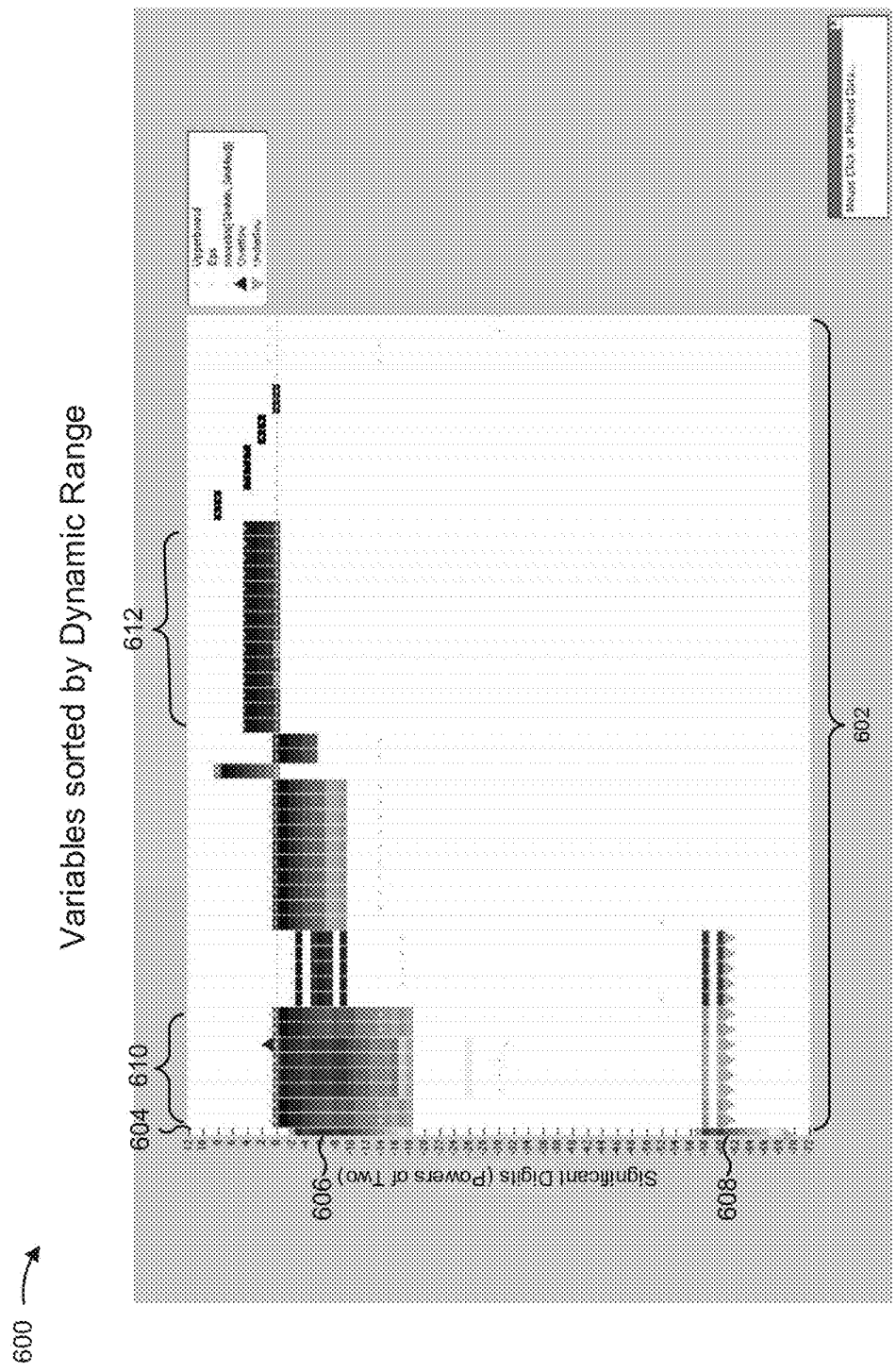
FIGS. 6A-6F are diagrams of an example implementation for interacting with a visualization of data types.

A user may interact with the visualization to manipulate a display of data in the visualization. The user may provide input to cause TCE 220 to sort and/or manipulate the visualization to change the ordering of columns, to include different subsets of variables, etc. For example, FIG. 6A shows a visualization of variables sorted by dynamic range. Columns 602 to the left of the visualization (e.g., columns indicated by reference number 610) represent variables that have a greater dynamic range of values than columns 602 to the right of the visualization (e.g., columns indicated by reference number 612). For example, a leftmost column 604 shows a shaded portion 606 starting from right below 0 as well as a shaded portion 608 below shaded portion 606. Each column 602 to the right of leftmost column 604 shows shaded portions that extend over a range that is less than that of leftmost column 604, as shown using shaded regions with a smaller height.

Figure 6B:
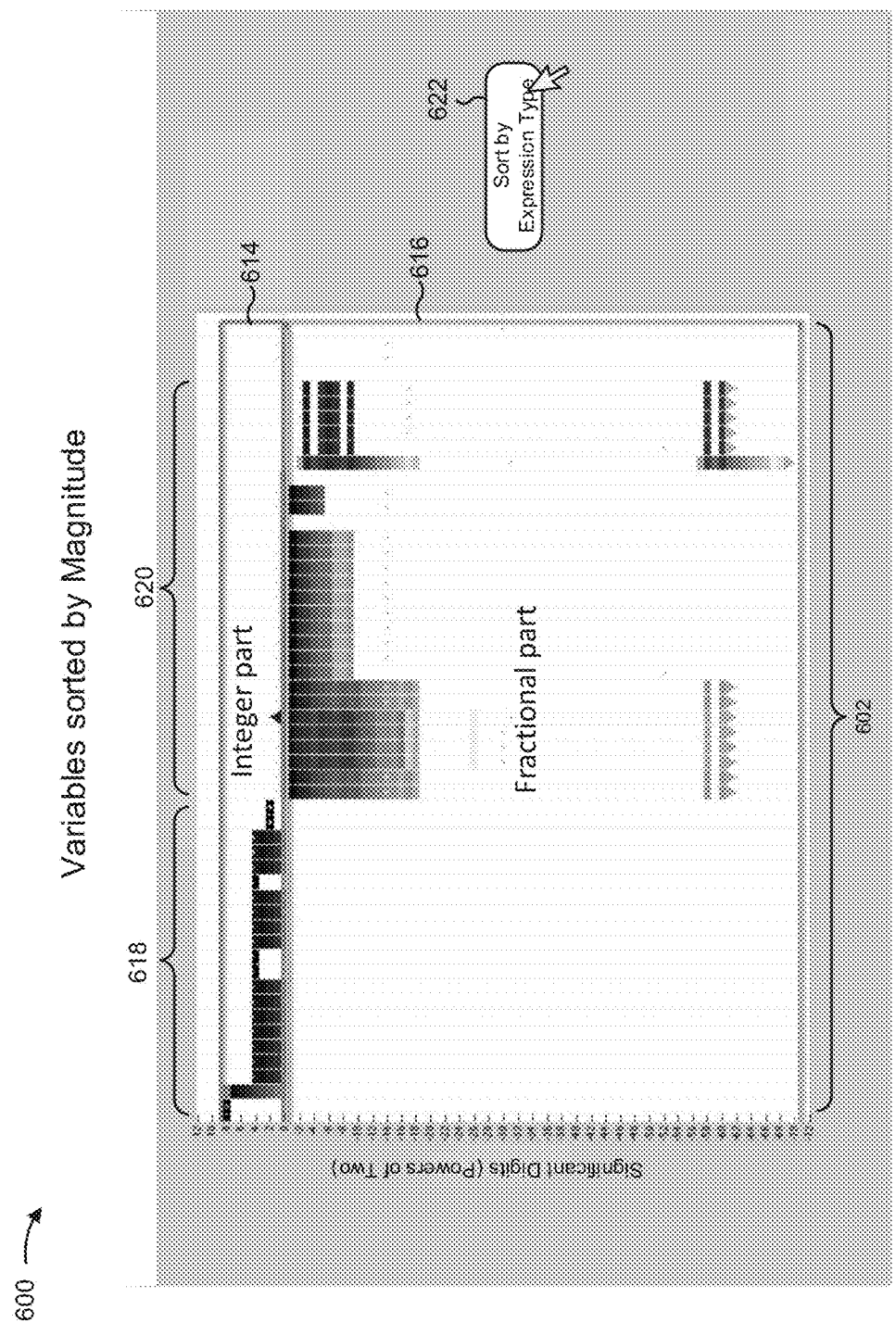

FIG. 6B shows another example sorting of the visualization of example implementation 600. For the purpose of FIG. 6B, assume that the user interacts with an input mechanism to sort the variables by magnitude. As shown, columns 602 are sorted by magnitude of values represented by the variables. Columns 602 to the left of the visualization (e.g., columns indicated by reference number 618) represent variables that represent values with a greater absolute value than columns 602 to the right of the visualization (e.g., columns indicated by reference number 620). The visualization may present this information with columns 602 on the left having shaded portions that extend higher than columns 602 on the right, as higher magnitude values would use more significant digits to the left of a decimal point.

FIG. 6B also shows that the columns 602 may provide information relating to integer and fractional parts of values represented by each variable. For example, shaded portions above 0 (e.g., as shown by a box with reference number 614) may indicate integer parts of values, while shaded portions below 0 (e.g., as shown by a box with reference number 616) may indicate fractional parts of values. Columns 602 without shaded portions below 0 (e.g., columns 618) may indicate that the variables may be assigned a data type for whole numbers. Conversely, columns 602 without shaded portions above 0 (e.g., columns 620) may indicate variables that represent only fractional values. Assume that the user interacts with a "Sort by Expression Type" button 622.

Figure 6C:
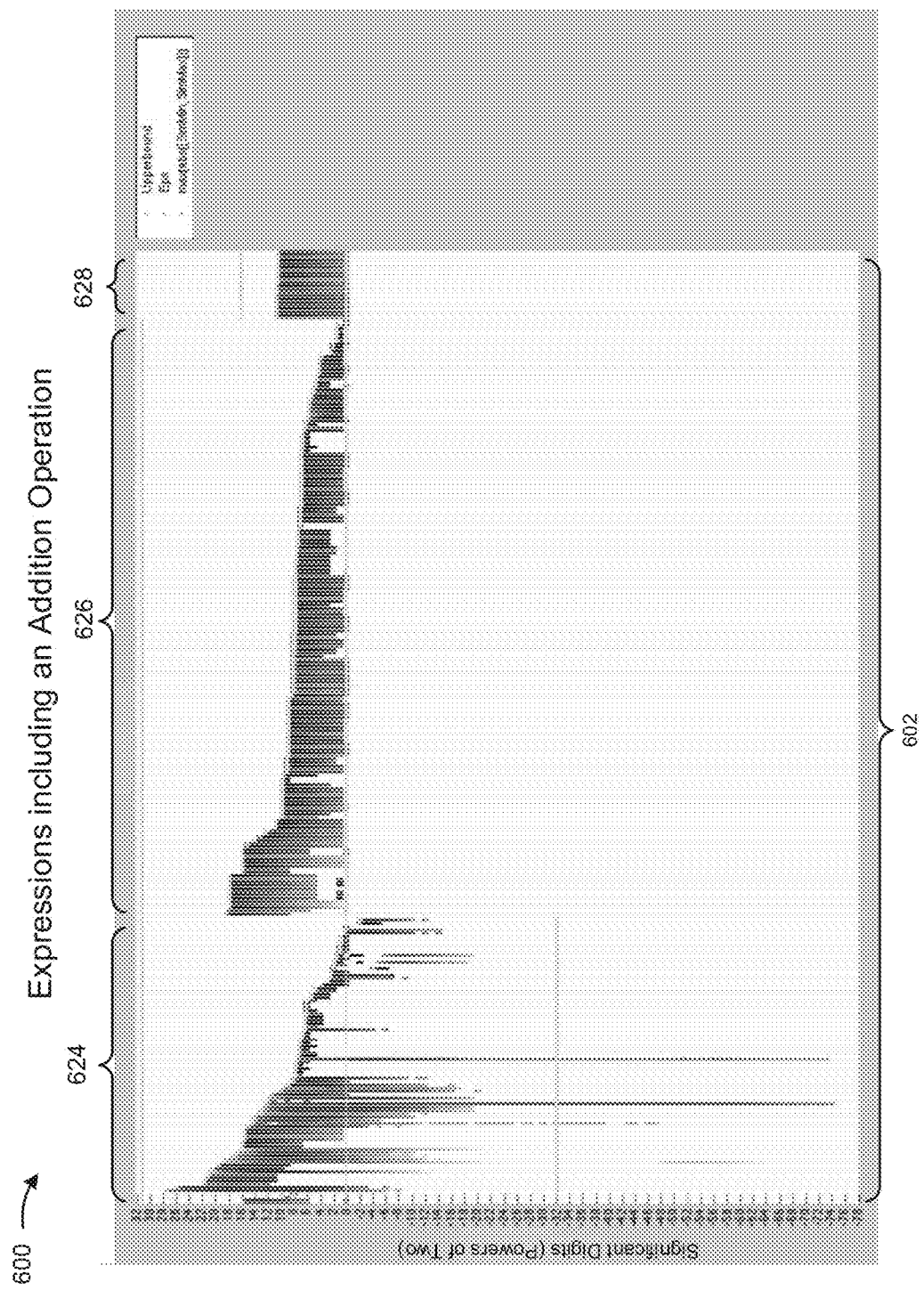

FIG. 6C shows another example sorting of the visualization of example implementation 600. Assume that the user interaction with the "Sort by Expression Type" button 622 causes TCE 220 to sort the variables by magnitude, as shown. The visualization of FIG. 6C shows expressions that include an addition operation in the expression. For example, an expression such as "acc+b(j)*z(k)" may be represented by one of columns 602 in the visualization because this expression includes an addition operation. The visualization may also be further sorted by one or more additional criteria. For example, columns 602 of FIG. 6C are also sorted by columns representing variables with both integer and fractional parts (as shown by reference number 624), then 32-bit integers (as shown by reference number 626), and then 16-bit integers (as shown by reference number 628). Each of the subsets are also in turn sorted by magnitude of values represented by the variables.

Figure 6D:
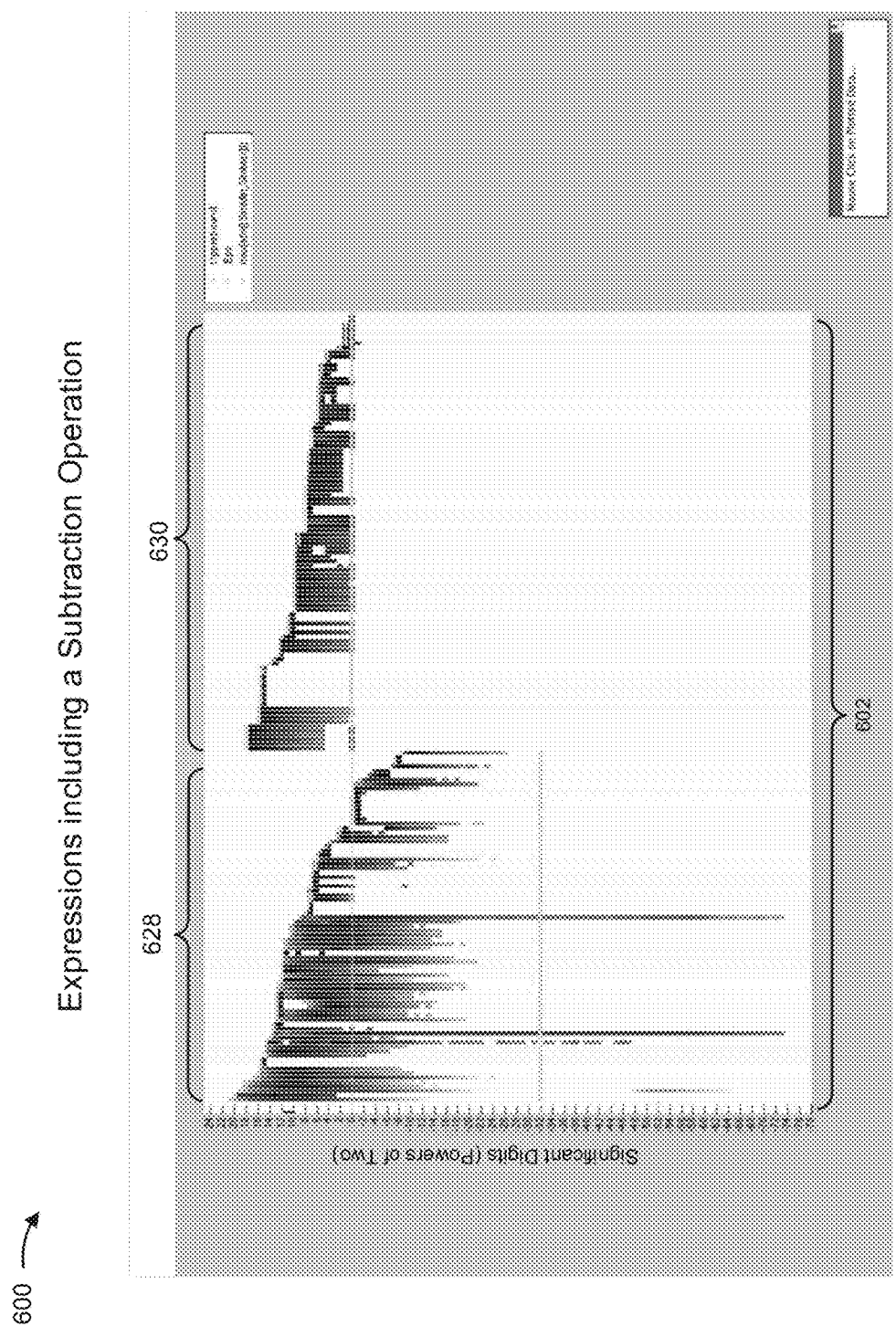

FIG. 6D shows another example sorting of the visualization of example implementation 600. In the example of FIG. 6D, the visualization shows expressions that include a subtraction operation. Again, columns 602 are further sorted by additional criteria such as whether the expressions include fractional parts (e.g., columns indicated by reference number 628) or not (e.g., columns indicated by reference number 630), as well as magnitude.

Figure 6E:
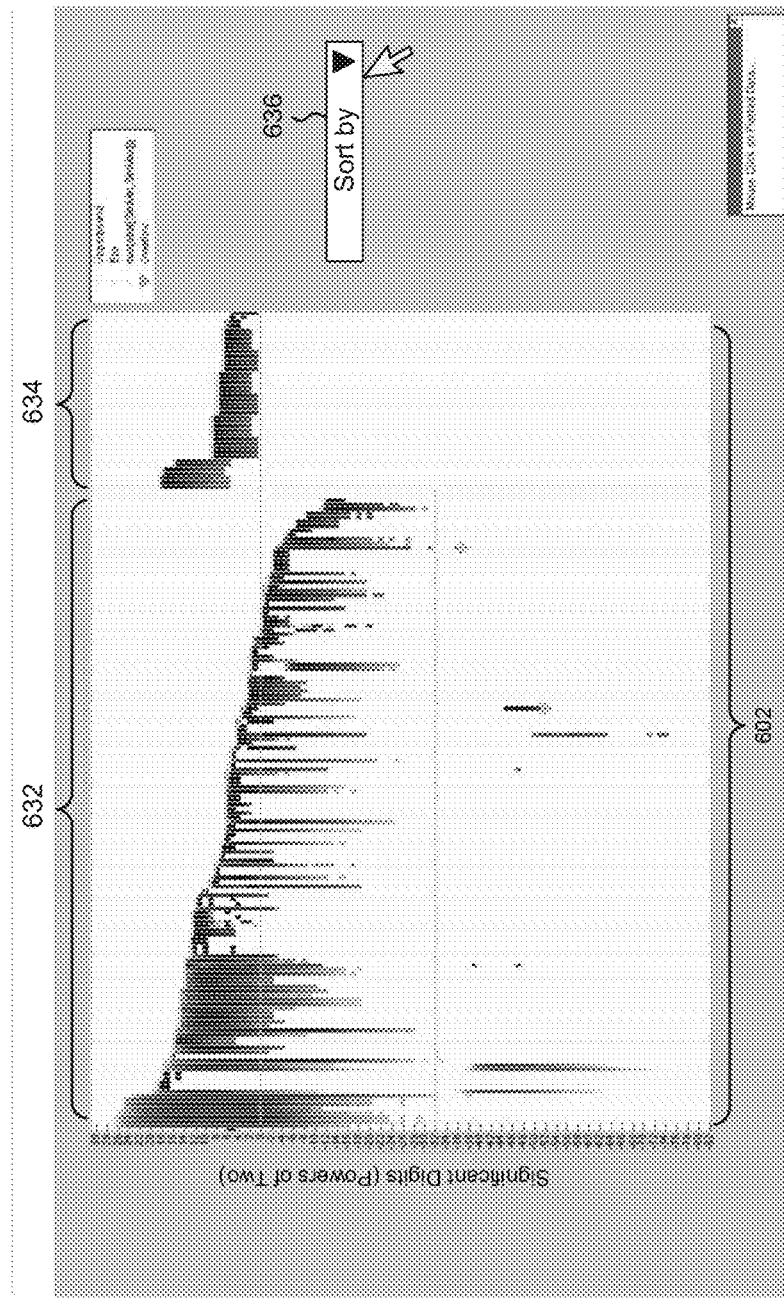

FIG. 6E shows another example sorting of the visualization of example implementation 600. In the example of FIG. 6E, the visualization shows expressions that include a multiplication operation. Again, columns have been shown sorted by expressions including fractional parts (e.g., columns indicated by reference number 632) and not (e.g., columns indicated by reference number 634) as well as magnitude. Assume that the user interacts with a "Sort by" dropdown menu 636 and selects a menu option to sort the visualization by expressions including a division operation.

Figure 6F:
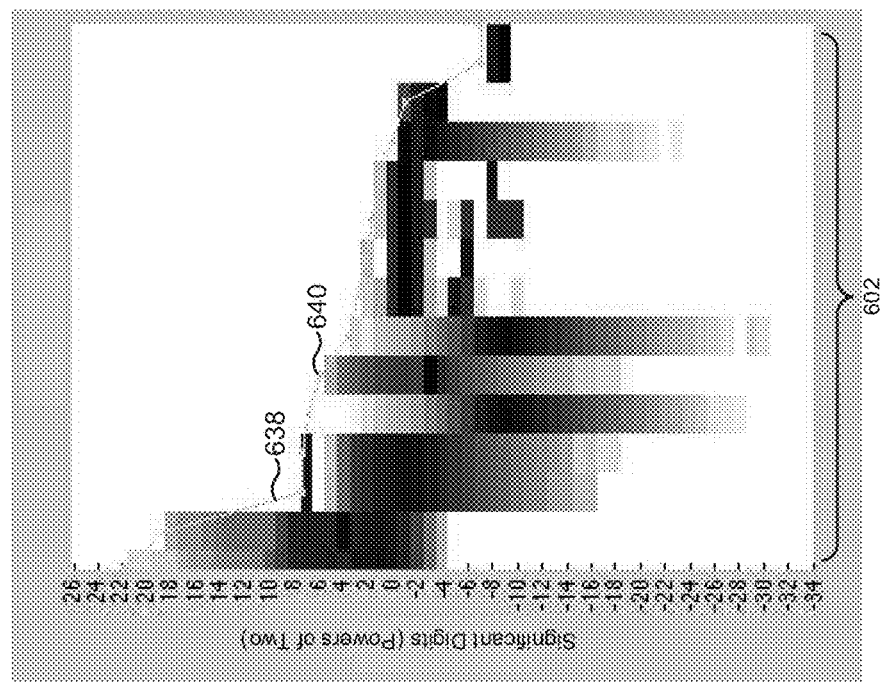

FIG. 6F shows another example sorting of the visualization of example implementation 600. Assume that the user interaction with the "Sort by" dropdown menu 636 causes TCE 220 to show expressions that include a division operation, as shown. The visualization also includes a line 638 connecting indicators 640 displaying a maximum value represented by each of the expressions.

As indicated above, FIGS. 6A-6F are provided merely as an example. Other examples are possible and may differ from what was described with regard to FIGS. 6A-6F. For example, the visualization may be sorted by data type or any other characteristic of the variables and/or expressions. The visualization may also be sorted based on test cases used in executing the code. The visualization may also be sorted based on order of occurrence of the variables, such as in the code and/or during execution. The visualization may also be sorted based on analysis of the code, such as excluding variables that have been proven error-free. The visualization may also be sorted to include other operations and/or functions, such as mathematical functions or other data processing functions, such as concatenation for string variables.

In some embodiments, the manipulation and sorting may be implemented by providing interfaces on the visualization for user input. For example, the user may be able to select through menu options or click on (e.g., with a mouse) axes or table keys of the visualization to sort the columns.

Figure 7:
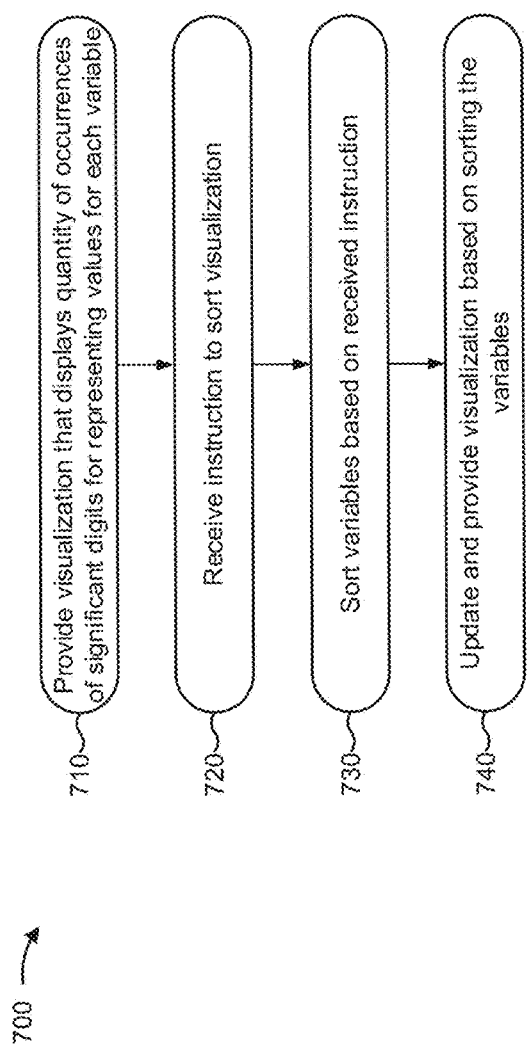
FIG. 7 is a flow chart of an example process for interacting with a visualization of data types.

FIG. 7 is a flow chart of an example process 700 for interacting with a visualization of data types. In some implementations, one or more process blocks of FIG. 7 may be performed by client device 210. In some implementations, one or more process blocks of FIG. 7 may be performed by another device or a group of devices separate from or including client device 210, such as server device 230.

As shown in FIG. 7, process 700 may include providing a visualization that displays a quantity of occurrences of significant digits for representing values for each variable (block 710). For example, the visualization may include histograms, such as example implementation 600 described in FIGS. 6A-6F. The visualization may be provided by generating the visualization from analyzing a portion or entirety of code and presenting the visualization for display via a user interface. In some implementations, information may be received about the variables and/or expressions, rather than the portion or entirety of code. For example, data structures including information associated with the variables and simulated values may be received, and the visualization may be generated from the received data structures. In some implementations, client device 210 may receive the visualization and provide the visualization for presentation.

As further shown in FIG. 7, process 700 may include receiving an instruction to sort the visualization (block 720). For example, client device 210 may sort the visualization based on similar characteristics. Characteristics may include features based on values represented by variables of the visualization, such as a dynamic range of the values for the variables, a representable range of the variables, a precision of the variables, a magnitude of values represented by the variables as described above, and/or other features. Characteristics may also include features based on the variables and/or expressions, such as a location in the code where the variable is found (e.g., variables in a function, a file, a workspace, etc.), whether the expression includes a particular operation (e.g., addition, subtraction, etc.), data types assigned to the variables, and/or other features. Sorting may also include filtering, for example, showing a subset of the variables (e.g., based on characteristics, such as variables including an overflow, etc.)

As further shown in FIG. 7, process 700 may include sorting variables based on the received instruction (block 730). Sorting variables may include changing an order of histograms, columns, or other representations of the variables in the visualization. Sorting may also include selecting a subset of variables to display on the visualization. Client device 210 may sort the visualization on more than one characteristic, such as a primary sort order based on a first characteristic and then a secondary sort order based on a second characteristic. Client device 210 may also sort the visualization by selecting a subset of variables based on a first characteristic (e.g., magnitude, data type, dynamic range, etc.) and ordering the variables based on a second characteristic (e.g., a characteristic other than the first characteristic).

As further shown in FIG. 7, process 700 may include updating and providing the visualization based on sorting the variables (block 740). The visualization may also be updated to indicate the criteria used in sorting the variables and provide one or more interfaces for the user to further or differently sort or manipulate the visualization.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8A:
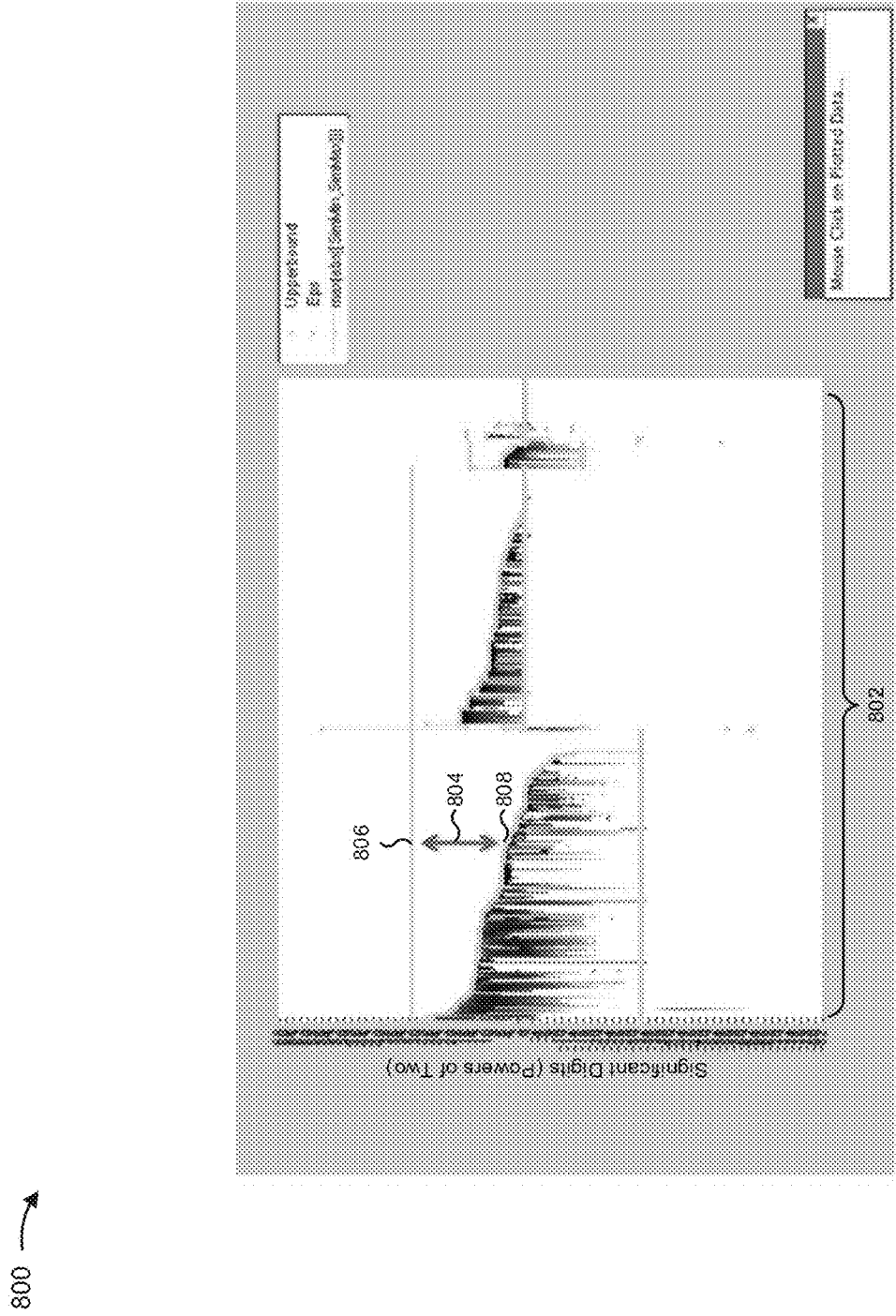
FIGS. 8A-8D are diagrams of another example implementation for interacting with a visualization of data types.

FIGS. 8A-8D are diagrams of an example implementation 800 for interacting with a visualization of data types. FIG. 8A shows a visualization that may be provided for display, e.g., via a user interface of client device 210. As described above, each column 802 of the visualization may represent a variable (and/or an expression). A user may interact with the visualization to manipulate underlying code on which the visualization is based. For example, client device 210 may provide an input mechanism via which the user may change code that determines characteristics of the variables. For example, FIG. 8A shows variables to which more integer bits have been assigned than are used by values represented by the variables in a simulation of the code. An arrow 804 shows a difference between a most significant digit allowed by a data type assigned to the variable and a most significant digit used by values represented by the variable. Such a sorting of the visualization may allow the user to determine which variables may be modified, such as assigning a different data type and/or a different word length to the variables.

Client device 210 may provide an input mechanism that allows the user to modify the code by interacting with the visualization. For example, the user may select and drag an indicator 806 that identifies a most significant digit allowed by a data type to match, or be closer to, an indicator 808 that identifies a most significant digit used by values represented by a variable. When the user modifies a location of indicator 806 on the visualization, client device 210 may modify the underlying code to reflect the new location of indicator 806.

For example, client device 210 may modify a portion of the code to assign a different data type and/or word length to the variable. In some implementations, client device 210 may provide an input mechanism for the user to modify some or all of indicators 806 of most significant digits allowed. For example, client device 210 may provide a mechanism for the user to match indicators 806 with indicators 808 of most significant digit. used Additionally, or alternatively, client device 210 may provide a mechanism for the user to set indicators a specified distance (e.g., one bit, a percentage of used bits, halfway between a current most significant digit allowed and used, a closest of predetermined set points, etc.) from indicators 808. In some implementations, client device 210 may provide similar interfaces for a least significant digit allowed and used for the variables as well as other characteristics of the variables.

Figure 8B:
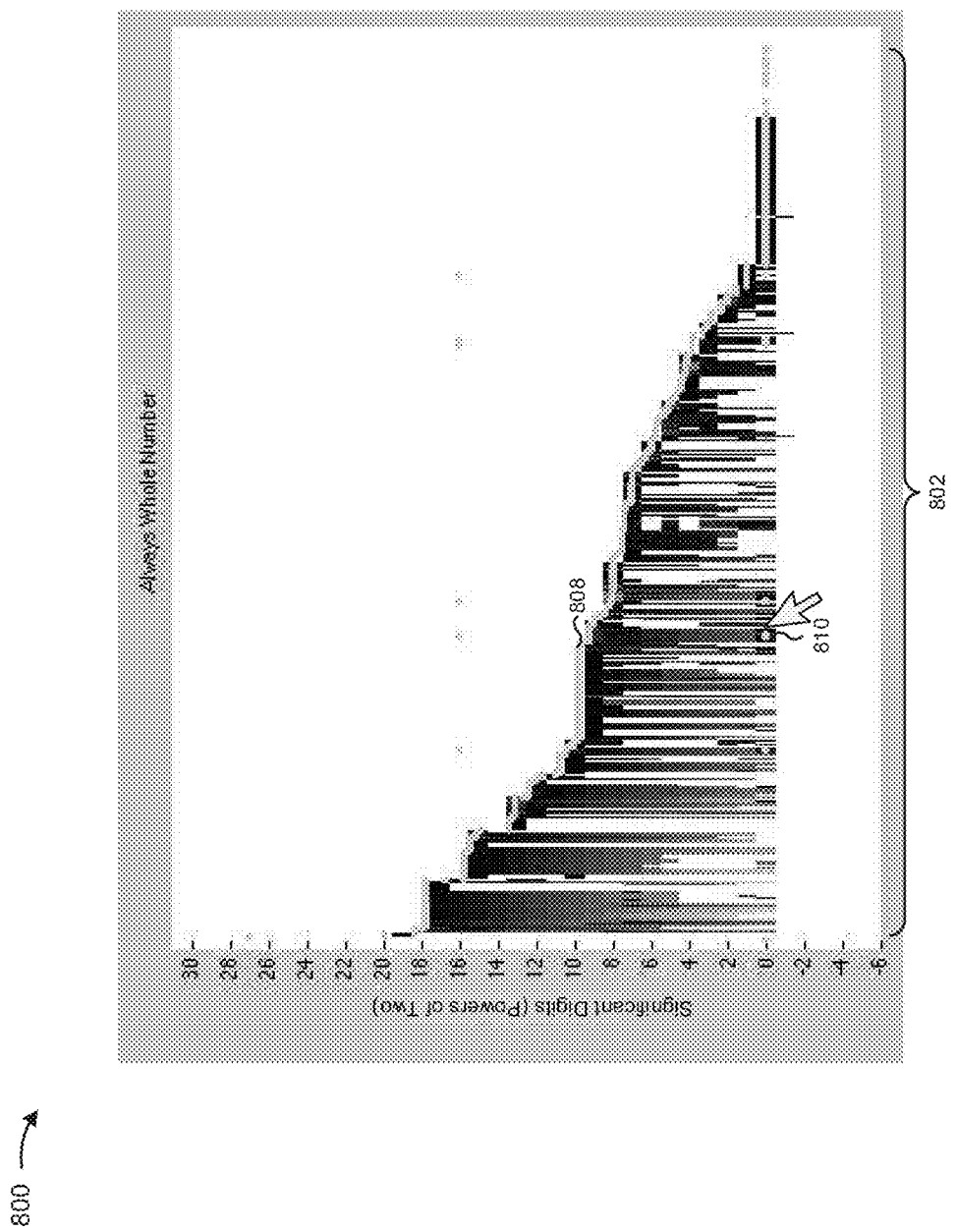

FIG. 8B shows columns 802 of the visualization have been sorted to display variables that represent only whole numbers. As none of the columns 802 extend below zero, fractional parts are not used by the values represented by the variables shown in FIG. 8B. Thus, for example, the user may interact with the visualization to instruct client device 210 to modify the code to assign the variables an integer data type. For example, the user may select and drag an indicator 810 of least significant digit allowed to 0 (corresponding to $2^0$). Alternatively, or additionally, client device 210 may provide an interface through which the user may assign specific data types to some or all of the variables in the visualization. For example, a user may make a selection and a dialog window may open. The window may include input fields, predetermined selections, etc., that the user can select. Once selected, a change may be applied to some or all variables in the visualization.

Figure 8C:
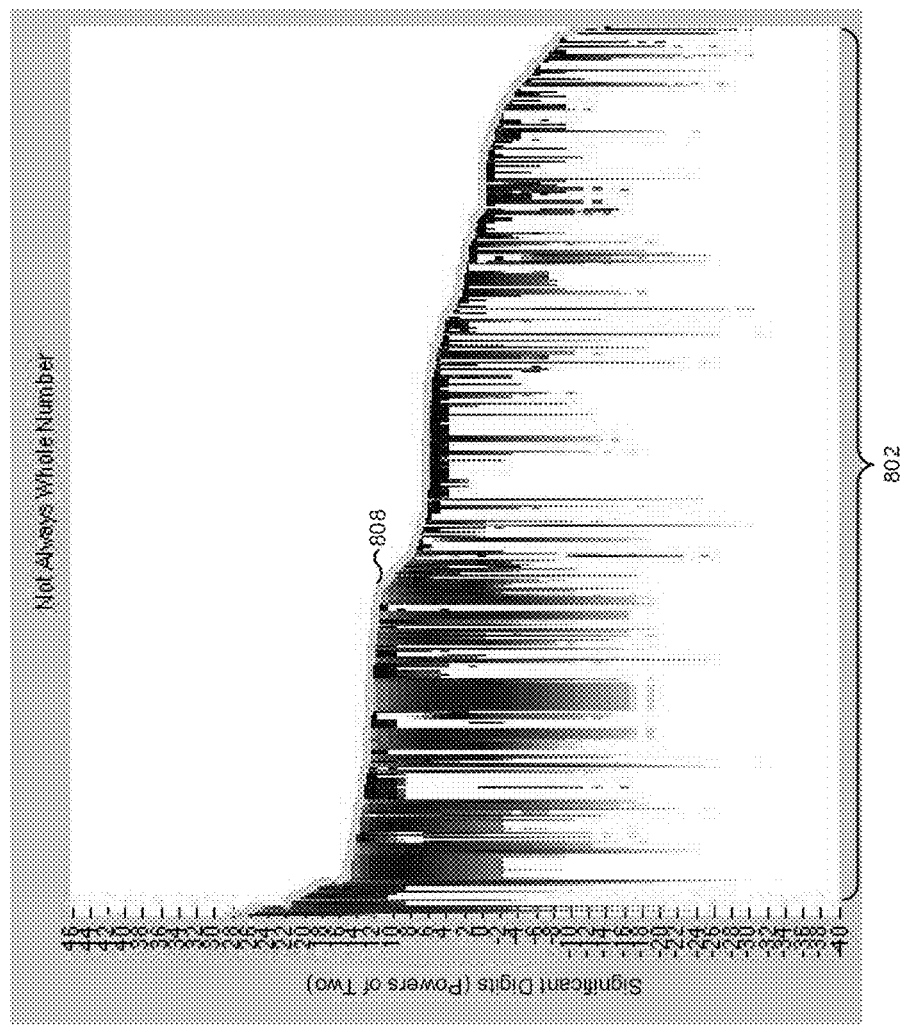

FIG. 8C shows an example visualization sorted to display variables that represent values that include fractional parts. While some of the columns also include whole numbers, client device 210 may further sort the visualization (e.g., by a least significant digit used) to display variables that include fractional values. The user may interact with the visualization, such as modifying locations of indicators of a least significant digit allowed, to instruct client device 210 to modify the underlying code.

Figure 8D:
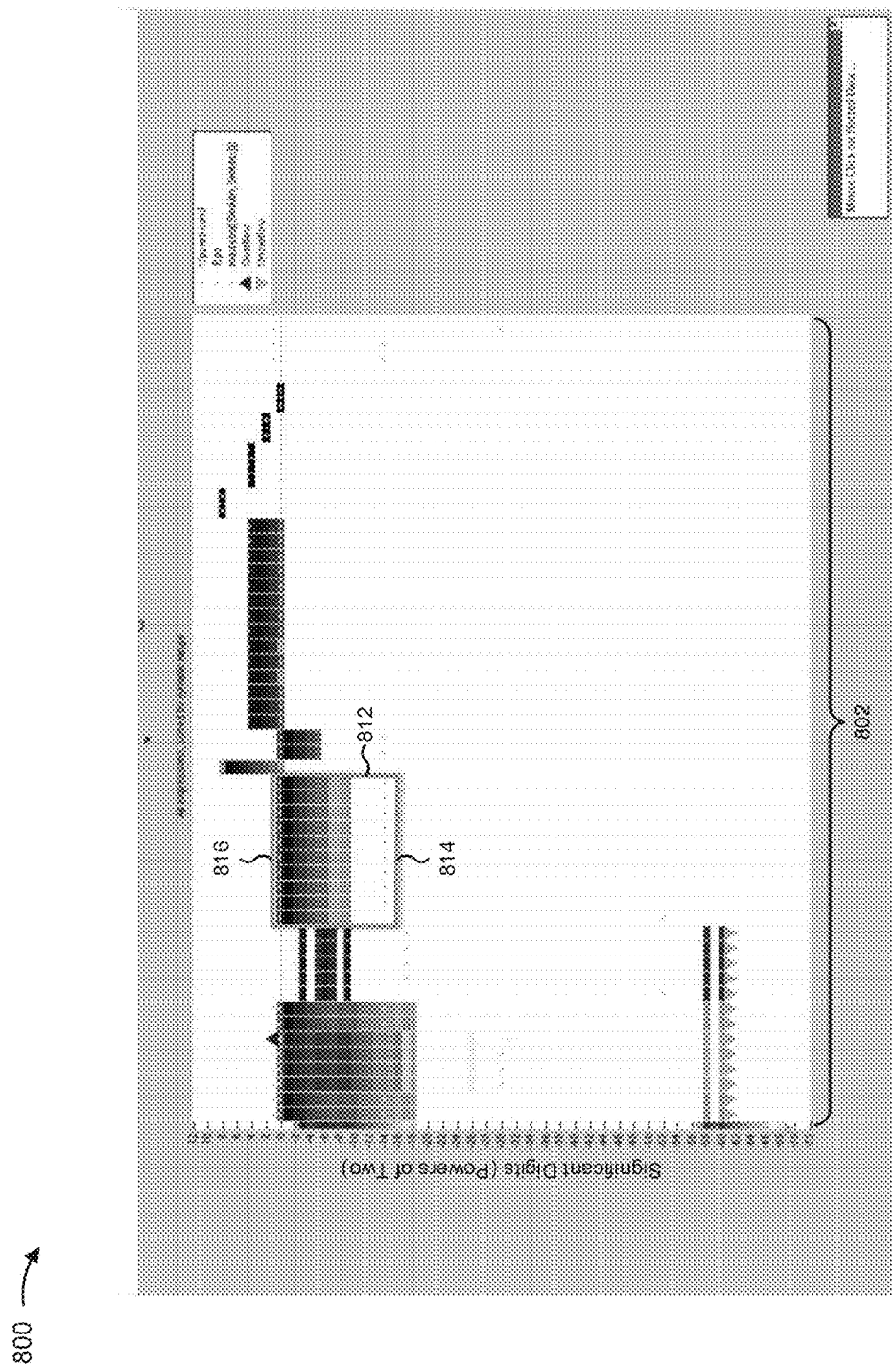

FIG. 8D shows an example visualization sorted by dynamic range. A subset of columns, indicated by reference number 812, may have a similar dynamic range. Client device 210 may allow a user to select a group of columns and modify the variables of the selected group. For example, the user may select and drag a selection rectangle to select a group of columns. The user may interact with the selection, such as by moving a bottom line 814 of the selection rectangle to indicate a modifying of least significant digit allowed for the selected columns. In some implementations bottom line 814 may represent a minimum value threshold. Additionally, a top line 816 may represent a maximum value threshold. In some implementations, selected columns may be modified as a group through interactions with one of the columns of the group. For example, modifying of one of the indicators in subset 810 may cause corresponding indicators in other columns of subset 810 to be modified. Subsets of columns may include columns that are adjacent and that are not adjacent to each other.

As indicated above, FIGS. 8A-8D are provided merely as an example. Other examples are possible and may differ from what was described with regard to FIGS. 8A-8D.

Figure 9:
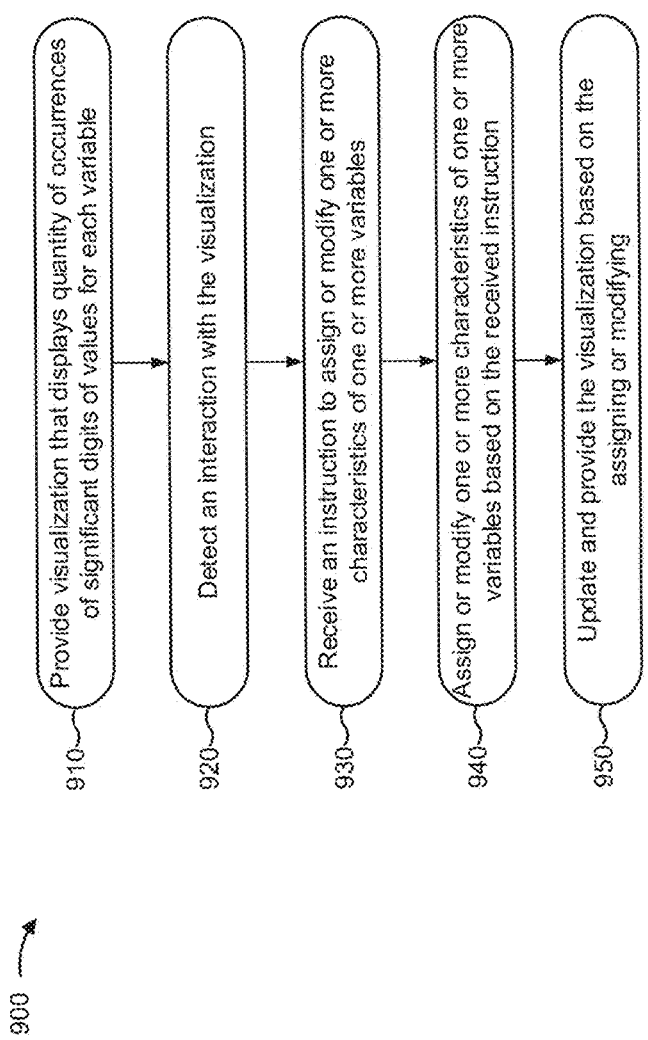
FIG. 9 is a flow chart of another example process for interacting with a visualization of data types.

FIG. 9 is a flow chart of an example process 900 for interacting with a visualization of data types. In some implementations, one or more process blocks of FIG. 9 may be performed by client device 210. In some implementations, one or more process blocks of FIG. 9 may be performed by another device or a group of devices separate from or including client device 210, such as server device 230.

As shown in FIG. 9, process 900 may include providing a visualization that displays a quantity of occurrences of significant digits of values for each variable (block 910). For example, the visualization may include histograms, such as example implementation 800 described in FIGS. 8A-8D.

As further shown in FIG. 9, process 900 may include detecting an interaction with the visualization (block 920). For example, client device 210 may provide an input mechanism that permits a user to interact with the visualization, and client device 210 may detect an interaction with the input mechanism. For example, interactions may include selecting, clicking with a mouse or pointer, dragging, moving, etc., an indicator, a column, or another interface on the visualization. For example, an interaction with the visualization may include selecting and dragging an upper-bound indicator, grouping multiple columns of the visualization, etc.

As further shown in FIG. 9, process 900 may include receiving an instruction to assign or modify one or more characteristics of one or more variables (block 930). For example, the one or more instructions may be received based on the interaction with the visualization. For example, a repositioning of a lower-bound indicator may indicate an instruction to modify a characteristic of a variable, such as modifying a data type and/or increasing or decreasing a word size of a variable represented by a column including the repositioned lower-bound indicator. As another example, receiving an instruction may include receiving a selection of one or more representations of variables in the interface along with a selection of a menu option indicating an assignment or modification of a characteristic of the selected one or more variables.

As further shown in FIG. 9, process 900 may include assigning or modifying one or more characteristics of one or more variables based on the received instruction (block 940). Client device 210 may assign or modify one or more characteristics of the one or more variables, for example, by changing code that corresponds to the one or more variables. For example, based on an instruction received to modify a data type of a variable, client device 210 may change one or more lines of code that initially assign a data type to the variable so that the variable is assigned the data type as indicated by the received instruction. In some implementations, assigning or modifying one or more characteristics of one or more variables may include modifying tables and/or other data structures associated with the one or more variables. For example, data types and/or other characteristics of the one or more variables may be stored in a table, which may be modified based on the received instruction.

As further shown in FIG. 9, process 900 may include updating and providing the visualization based on the assigning or modifying (block 950). Client device 210 may update the visualization to reflect the assigned or modified one or more characteristics of the one or more variables and provided for display to the user.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

Figure 10:
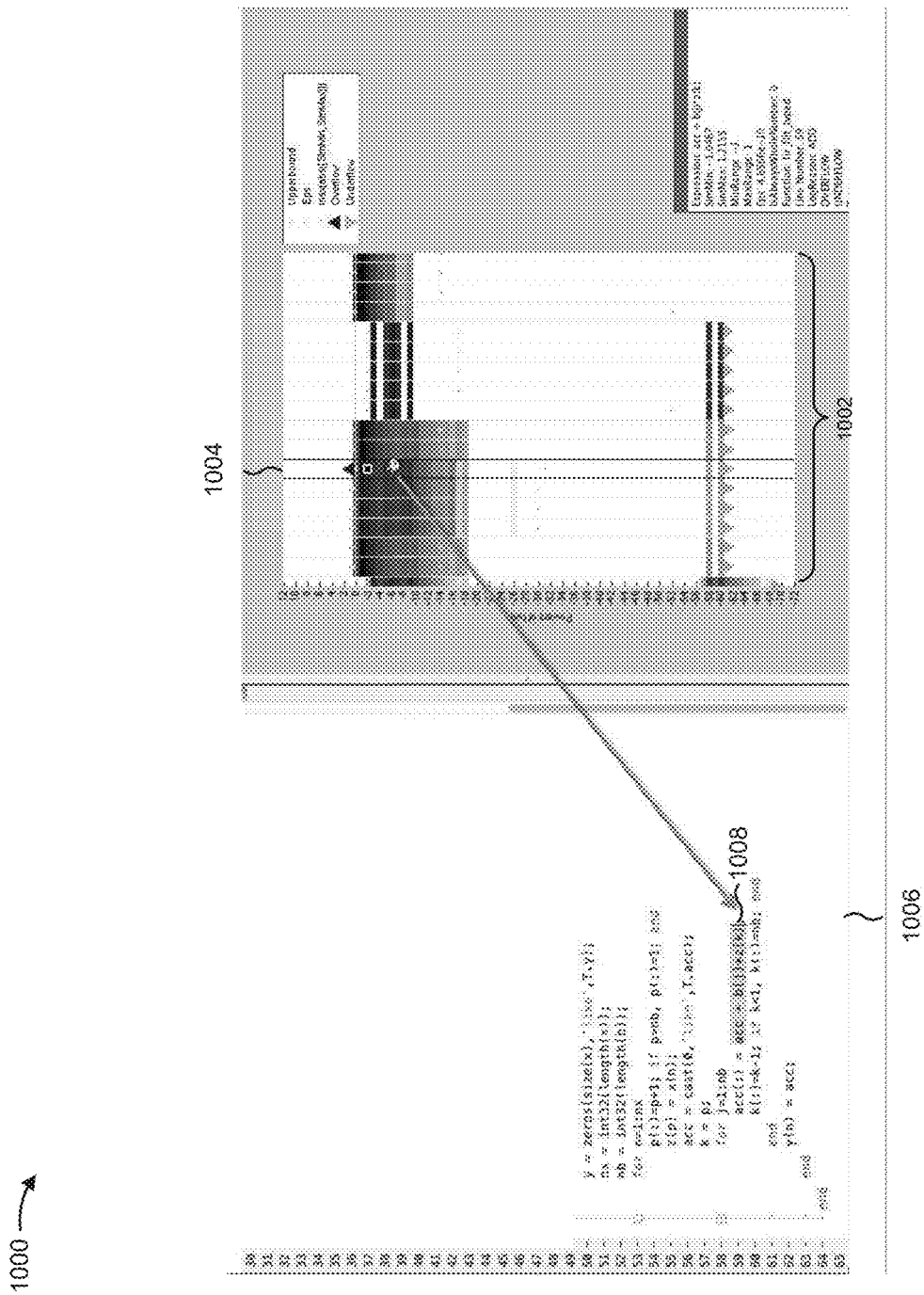
FIG. 10 is a diagram of another example implementation for interacting with a visualization of data types.

FIG. 10 is a diagram of an example implementation 1000 for interacting with a visualization of data types. As described above, each column 1002 of the visualization may represent a variable (and/or an expression). A user may interact with the visualization to be directed to underlying code on which the visualization is based. In some embodiments, the underlying code may include code generated from a model (e.g., by a code generator).

For example, a column 1004 may represent an expression such as "acc+b(j)*z(k)." A user may interact with column 1004, such as by selecting (e.g., double-clicking) column 1004. Based on the interaction with column 1004, a code window 1006 of the interface may display a code portion 1008 that includes the expression. As shown in example implementation 1000, client device 210 may highlight code portion 1008.

In some implementations, client device 210 may hide code window 1006 until the user interacts with a column to request a display of related underlying code. In some implementations, client device 210 may display multiple instances of the expression in different code portions. For example, the user may interact with the column again in a similar or different manner to jump to a next occurrence of the expression. Alternatively, or additionally, the user may interact with an input mechanism so the user may jump to a next occurrence of the expression. Alternatively, or additionally, code window 1006 may show multiple code portions simultaneously, for example, by splitting code window 1006 into multiple partitions.

In some implementations, the user may further interact with a column, such as described above with reference to FIGS. 8A-8D. Client device 210 may update code window 1006 to reflect modifications to the code based on interactions by the user with the column. For example, the user may assign or modify a data type by interacting with a corresponding column. Code window 1006 may update to display changes in code that reflect the assigning or modifying of the data type. In some implementations, client device 210 may highlight or otherwise accentuate the changes in the code to indicate where the changes have been made. In some implementations, interactions by the user with the column may affect portions of code not currently shown in the code window 1006. In some implementations, client device 210 may update other affected portions of code and indicate such changes have been made, for example, by providing an indicator that other portions of code may have been affected and/or displaying the other portions of code.

In some implementations, the user may change code directly in code window 1006. Client device 210 may update corresponding portions of the visualization to reflect the changes in the code. Client device 210 may highlight or otherwise accentuate changes to corresponding portions of the visualization to indicate the changes.

As indicated above, FIG. 10 is provided merely as an example. Other examples are possible and may differ from what was described with regard to FIG. 10.

FIG. 11 is a flow chart of an example process 1100 for interacting with a visualization of data types. In some implementations, one or more process blocks of FIG. 11 may be performed by client device 210. In some implementations, one or more process blocks of FIG. 11 may be performed by another device or a group of devices separate from or including client device 210, such as server device 230.

As shown in FIG. 11, process 1100 may include providing a visualization that displays a quantity of occurrences of significant digits of values for each variable (block 1110). For example, the visualization may include histograms such as example implementation 1000 described in FIG. 10.

As further shown in FIG. 11, process 1100 may include detecting an interaction with the visualization (block 1120). Interactions with the visualization may include user input received on the visualization. For example, interactions may include selecting, clicking with a mouse or pointer, double clicking, dragging, moving, etc., of indicators, columns, or other input mechanisms on the visualization.

As further shown in FIG. 11, process 1100 may include receiving one or more instructions to display a portion of code associated with a portion of the visualization (block 1130). The one or more instructions received may be based on the interaction with the visualization detected. The portion of code associated with the portion of the visualization may include an occurrence of a variable or expression represented by the portion of the visualization. In some implementations, the portion of code may be otherwise associated with the portion of the visualization. For example, an interaction with an overflow indicator on the visualization may instruct client device 210 to display a portion of code where the overflow occurs.

As further shown in FIG. 11, process 1100 may include displaying the portion of the code (1140). As described above, the portion of code may be displayed in a code window. In some implementations, client device 210 may show the portion of code in a text box, for example, in response to a cursor hovering over a portion of the visualization. Alternatively, or additionally, other such displays may be implemented to display the portion of code associated with the portion of the visualization.

Although FIG. 11 shows example blocks of process 1100, in some implementations, process 1100 may include additional blocks, fewer blocks, different blocks, or differently arranged blocks than those depicted in FIG. 11. Additionally, or alternatively, two or more of the blocks of process 1100 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Program code (sometimes referred to herein as code) is to be broadly interpreted to include text-based code that may not require further processing to execute (e.g., C++ code, Hardware Description Language (HDL) code, very-high-speed integrated circuits (VHSIC) HDL (VHDL) code, Verilog code, Java code, another type of hardware and/or software based code that may be compiled and/or synthesized, etc.), binary code that may be executed (e.g., executable files that may be directly executed by an operating system, bitstream files that may be used to configure an FPGA, Java byte code, object files combined together with linker directives, source code, makefiles, etc.), text files that may be executed in conjunction with other executables (e.g., Python text files, Octave files, a collection of dynamic-link library (DLL) files with text-based combining, configuration information that connects pre-compiled modules, an extensible markup language (XML) file describing module linkage, etc.), source code (e.g., readable by a human), machine code (e.g., readable by a machine), graphical models, or the like. In some implementations, code may include different combinations of the above-identified classes of code (e.g., text-based code, binary code, text files, source code, machine code, etc.). Additionally, or alternatively, code may include code generated using a dynamically-typed programming language (e.g., the M language, a MATLAB® language, a MATLAB-compatible language, a MATLAB-like language, etc.) that may be used to express problems and/or solutions using mathematical notations. Additionally, or alternatively, code may be of any type, such as a function, a script, an object, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

TCE 220 may provide a computing environment that may allow, for example, a user to perform tasks related to disciplines, such as, but not limited to, mathematics, science, engineering, medicine, business, biology, finance, etc. TCE 220 may use an array as a basic element, where the array may not require dimensioning. These arrays may be used to support array-based programming where an operation may apply to an entire set of values included in the arrays. Array-based programming may allow array-based operations to be treated as high-level programming that may allow, for example, operations to be performed on entire aggregations of data without having to resort to explicit loops of individual non-array operations.

TCE 220 may include a programming language (e.g., the MATLAB language) that may be used to express problems and/or solutions in mathematical notations. The programming language may be dynamically typed and/or array-based. In a dynamically typed array-based computing language, data may be contained in arrays and data types of the data may be determined (e.g., assigned) at program execution time.

For example, suppose a program, written in a dynamically typed array-based computing language, includes the following statements:
A='hello'
A=int32([1, 2])
A=[1.1, 2.2, 3.3]

Now suppose the program is executed, for example, in a TCE, such as TCE 220. During run-time, when the statement "A='hello'" is executed the data type of variable "A" may be a string data type. Later when the statement "A=int32([1, 2])" is executed the data type of variable "A" may be a 1-by-2 array containing elements whose data type are 32 bit integers. Later, when the statement "A=[1.1, 2.2, 3.3]" is executed, since the language is dynamically typed, the data type of variable "A" may be changed from the above 1-by-2 array to a 1-by-3 array containing elements whose data types are floating point. As can be seen by this example, data in a program written in a dynamically typed array-based computing language may be contained in an array. Moreover, the data type of the data may be determined during execution of the program. Thus, in a dynamically type array-based computing language, data may be represented by arrays and data types of data may be determined at run-time.

TCE 220 performs matrix and/or vector computations that may be used for data analysis, data visualization, application development, simulation, modeling, and/or algorithm development. These matrix and/or vector formulations may be used in many areas, such as, but not limited to, statistics, image processing, signal processing, control design, life sciences modeling, financial modeling, discrete event analysis and/or design, and state-based analysis and/or design.

TCE 220 provides mathematical routines and a high-level programming language suitable for non-professional programmers and may provide graphical tools that may be used for creating plots, surfaces, images, volumetric representations, or other representations. TCE 220 may provide these routines and/or tools using toolboxes (e.g., toolboxes for signal processing, image processing, data plotting, parallel processing, etc.). TCE 220 may also provide these routines in other ways, such as, for example, via a library, local or remote database (e.g., a database operating in a computing cloud), remote procedure calls (RPCs), and/or an application programming interface (API). Embodiments of TCE 220 may be configured to improve runtime performance when performing computing operations. For example, TCE 220 may include a just-in-time (JIT) compiler in an exemplary embodiment.

Examples of TCEs and/or TCE-like applications that may be adapted to implement one or more embodiments of the invention may include, but are not limited to applications that implement languages such as the MATLAB® environment available from The MathWorks, Inc.; GNU Octave from the GNU Project; Mathematica from Wolfram Research, Inc.; Mathcad from Mathsoft Engineering & Education Inc.; Maple from Maplesoft; Scilab from The French Institution for Research in Computer Science and Control (INRIA).

A code generator can generate code from a model. In an embodiment, the code generator may receive code in a first format and may transform the code from the first format into a second format. In an embodiment, the code generator can generate source code, assembly language code, binary code, interface information, configuration information, performance information, etc., from at least a portion of a graphical model.

For example, the code generator can generate C, C++, SystemC, Java, etc., from the graphical model. Embodiments of the code generator can further generate Unified Modeling Language (UML) based representations and/or extensions from some or all of a graphical model (e.g., System Modeling Language (SysML), Extensible Markup Language (XML), Modeling and Analysis of Real Time and Embedded Systems (MARTE), Hardware Description Language (HDL), Automotive Open System Architecture (AUTOSAR), etc.).

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A device, comprising:
   one or more hardware processors to:
      obtain program code;
      determine a plurality of variables based on the program code;
      at least one of:
         execute the program code; or
         analyze the program code;
      determine values of the plurality of variables based on the at least one of executing or analyzing of the program code;
      determine a range for each variable based on positions of at least one significant digit for the values,
         the range being determined based on a count of a quantity of occurrences of the at least one significant digit for the values;
      determine relationships between the plurality of variables based on the at least one of the executing or analyzing of the program code;
      determine one or more effects on the range for the plurality of variables based on the relationships between the plurality of variables;
      generate a visualization that presents the range for the plurality of variables, the relationships between the plurality of variables, and the one or more effects on the range for the plurality of variables; and
      provide the visualization for display.

2. The device of claim 1, where the one or more hardware processors are further to:
   determine relationships between the plurality of variables, a plurality of expressions, and a plurality of functions; and
   when generating the visualization, are to present the relationships between the plurality of variables, the plurality of expressions, and the plurality of functions.

3. The device of claim 2, where the one or more hardware processors, when presenting the relationships are to:
   aggregate two or more histograms representing ranges of two or more variables, expressions, or functions of the plurality of variables, the plurality of expressions, and the plurality of functions.

4. The device of claim 1, where the one or more hardware processors, when determining the relationships between the plurality of variables, are to:
  generate one or more intermediate representations including the plurality of variables; and
  analyze the one or more intermediate representations to determine measures of correlation between the plurality of variables.

5. The device of claim 4, where the one or more hardware processors are further to:
  detect an interaction with the visualization; and
  in response to the interaction, at least one of:
    display at least a portion of the one or more intermediate representations;
    display a portion of program code associated with a portion of the visualization; or
    assign or modify one or more characteristics of one or more of the plurality of variables.

6. The device of claim 5, where the one or more hardware processors, when assigning or modifying the one or more characteristics, are to:
  assign or modify a data type of the one or more of the plurality of variables.

7. The device of claim 5, where the one or more hardware processors, when assigning or modifying the one or more characteristics, are to:
  assign or modify one or more characteristics of one or more variables of the plurality of variables based on the measures of correlation between the one or more variables.

8. The device of claim 5, where the one or more hardware processors are further to:
  update the visualization based on assigning or modifying a data type of the one or more of the plurality of variables; and
  provide the visualization for display.

9. The device of claim 4, where the one or more hardware processors are further to:
  detect an interaction with the at least a portion of the one or more intermediate representations;
  update the visualization based on the interaction; and
  provide the visualization for display.

10. The device of claim 1, where the one or more hardware processors, when determining the relationships between the plurality of variables, are to:
  generate one or more intermediate representations including the plurality of variables, a plurality of expressions, and a plurality of functions; and
  analyze the one or more intermediate representations to determine measures of correlation between the plurality of variables, the plurality of expressions, and the plurality of functions.

11. A computer-readable medium storing instructions, the instructions comprising:
  one or more instructions that, when executed by one or more processors, cause the one or more processors to:
    obtain program code;
    determine a plurality of variables based on the program code;
    at least one of:
      execute the program code; or
      analyze the program code;
    determine values of the plurality of variables based on the at least one of executing or analyzing of the program code;
    determine a range for each variable based on positions of at least one significant digit for the values, the range being determined based on a count of a quantity of occurrences of the at least one significant digit for the values;
    determine relationships between the plurality of variables based on the at least one of the executing or analyzing of the program code;
    determine one or more effects on the range for the plurality of variables based on the relationships between the plurality of variables;
    generate a visualization that presents the range for the plurality of variables, the relationships between the plurality of variables, and the one or more effects on the range for the plurality of variables; and
    provide the visualization for display.

12. The computer-readable medium of claim 11, where the one or more instructions, when executed by the one or more processors further cause the one or more processors to:
  determine relationships between the plurality of variables, a plurality of expressions, and a plurality of functions; and
  when generating the visualization, are to present the relationships between the plurality of variables, the plurality of expressions, and the plurality of functions.

13. The computer-readable medium of claim 12, where the one or more instructions that cause the one or more processors to present the relationships, further cause the one or more processors to:
  aggregate two or more histograms representing ranges of two or more variables, expressions, or functions of the plurality of variables, the plurality of expressions, and the plurality of functions.

14. The computer-readable medium of claim 11, where the one or more instructions that cause the one or more processors to determine the relationships between the plurality of variables, further cause the one or more processors to:
  generate one or more intermediate representations including the plurality of variables; and
  analyze the one or more intermediate representations to determine measures of correlation between the plurality of variables.

15. The computer-readable medium of claim 14, where the one or more instructions, when executed by the one or more processors further cause the one or more processors to:
  detect an interaction with the visualization; and
  in response to the interaction, at least one of:
    display at least a portion of the one or more intermediate representations;
    display a portion of program code associated with a portion of the visualization; or
    assign or modify one or more characteristics of one or more of the plurality of variables.

16. The computer-readable medium of claim 15, where the one or more instructions that cause the one or more processors to assign or modify the one or more characteristics, further cause the one or more processors to:
  assign or modify a data type of the one or more of the plurality of variables.

17. The computer-readable medium of claim 15, where the one or more instructions that cause the one or more processors to assign or modify the one or more characteristics, further cause the one or more processors to:
  assign or modify one or more characteristics of one or more variables of the plurality of variables based on the measures of correlation between the one or more variables.

18. The computer-readable medium of claim 15, where the one or more instructions, when executed by the one or more processors further cause the one or more processors to:
  update the visualization based on assigning or modifying a data type of the one or more of the plurality of variables; and
  provide the visualization for display.

19. The computer-readable medium of claim 14, where the one or more instructions, when executed by the one or more processors further cause the one or more processors to:
  detect an interaction with the at least a portion of the one or more intermediate representations;
  update the visualization based on the interaction; and
  provide the visualization for display.

20. A method comprising:
  obtaining program code,
    the obtaining being performed by one or more devices;
  determining a plurality of variables based on the program code,
    the determining being performed by the one or more devices;
  at least one of:
    executing the program code,
      the executing being performed by the one or more devices; or
    analyzing the program code,
      the analyzing being performed by the one or more devices;
  determining values of the plurality of variables based on the at least one of executing or analyzing of the program code,
    the determining being performed by the one or more devices;
  determining a range for each variable based on positions of at least one significant digit for the values,
    the range being determined based on a count of a quantity of occurrences of the at least one significant digit for the values,
    the determining the range being performed by the one or more devices;
  determining relationships between the plurality of variables based on the at least one of the executing or analyzing of the program code,
    the determining the relationships being performed by the one or more devices;
  determining one or more effects on the range for the plurality of variables based on the relationships between the plurality of variables,
    the determining the one or more effects being performed by the one or more devices;
  generating a visualization that presents the range for the plurality of variables, the relationships between the plurality of variables, and the one or more effects on the range for the plurality of variables,
    the generating being performed by the one or more devices; and
  providing the visualization for display,
    the providing being performed by the one or more devices.

\* \* \* \* \*